(12) United States Patent
Dejima

(10) Patent No.: US 10,456,165 B2
(45) Date of Patent: Oct. 29, 2019

(54) ENDOSCOPIC SURGICAL DEVICE AND OVERTUBE

(71) Applicant: FUJIFILM Corporation, Tokyo (JP)

(72) Inventor: Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 280 days.

(21) Appl. No.: 15/275,471

(22) Filed: Sep. 26, 2016

(65) Prior Publication Data

US 2017/0007293 A1    Jan. 12, 2017

Related U.S. Application Data

(63) Continuation of application No. PCT/JP2015/059352, filed on Mar. 26, 2015.
(Continued)

(51) Int. Cl.
*A61B 1/00* (2006.01)
*A61B 17/34* (2006.01)
(Continued)

(52) U.S. Cl.
CPC ...... *A61B 17/3421* (2013.01); *A61B 1/00112* (2013.01); *A61B 1/00121* (2013.01);
(Continued)

(58) Field of Classification Search
CPC .................. A61B 1/00098; A61B 1/00154
See application file for complete search history.

(56) References Cited

U.S. PATENT DOCUMENTS

| 4,436,087 A | 3/1984 | Ouchi |
| 5,976,077 A | 11/1999 | Wittens et al. |

(Continued)

FOREIGN PATENT DOCUMENTS

| JP | S54081690 | 6/1979 |
| JP | H10094513 | 4/1998 |

(Continued)

OTHER PUBLICATIONS

"Written Opinion of the International Searching Authority of PCT/JP2015/059352", dated Apr. 28, 2015, with English translation thereof, pp. 1-8.
(Continued)

*Primary Examiner* — Aaron B Fairchild
(74) *Attorney, Agent, or Firm* — JCIPRNET

(57) ABSTRACT

An endoscopic surgical device and an overtube that allows the state of a distal end of a treatment tool to be easily checked while reducing the diameter of the overtube and can improve surgical efficiency. An endoscope insertion part of an endoscope and a treatment tool insertion part of a treatment tool are insertable through an overtube inserted into a body wall, and a slider is provided for moving the endoscope insertion part and the treatment tool insertion part forward and backward in an interlocking manner. A guide part that guides the endoscope insertion part in a direction away from a distal end of the treatment tool insertion part is provided in the vicinity of an endoscope delivery port in a distal end cap at the distal end of the overtube, and the endoscope insertion part is delivered in an oblique direction from the endoscope delivery port.

12 Claims, 17 Drawing Sheets

Related U.S. Application Data

(60) Provisional application No. 61/971,222, filed on Mar. 27, 2014.

(51) Int. Cl.
    *A61B 17/29*      (2006.01)
    *A61B 1/05*      (2006.01)
    *A61B 1/06*      (2006.01)

(52) U.S. Cl.
    CPC ...... *A61B 1/00128* (2013.01); *A61B 1/00135* (2013.01); *A61B 1/00154* (2013.01); *A61B 17/2909* (2013.01); *A61B 1/00018* (2013.01); *A61B 1/05* (2013.01); *A61B 1/0661* (2013.01); *A61B 2017/3445* (2013.01)

(56) References Cited

U.S. PATENT DOCUMENTS

| | | | |
|---|---|---|---|
| 2005/0119525 A1* | 6/2005 | Takemoto | A61B 1/00154 600/114 |
| 2011/0263937 A1 | 10/2011 | Korner et al. | |
| 2012/0095291 A1 | 4/2012 | Nakajima | |
| 2015/0080650 A1 | 3/2015 | Dejima et al. | |
| 2015/0230697 A1 | 8/2015 | Phee et al. | |

FOREIGN PATENT DOCUMENTS

| | | |
|---|---|---|
| JP | 2004121546 | 4/2004 |
| JP | 2008536552 | 9/2008 |
| JP | 2010511440 | 4/2010 |
| JP | 2011224376 | 11/2011 |
| JP | 5224305 | 7/2013 |
| WO | 2006110275 | 10/2006 |
| WO | 2008070556 | 6/2008 |
| WO | 2013176167 | 11/2013 |
| WO | 2014046618 | 3/2014 |

OTHER PUBLICATIONS

"Search Report of European Counterpart Application", dated Mar. 1, 2017, p. 1-p. 7.

"Office Action of Japan Counterpart Application," dated Aug. 31, 2017, with English translation thereof, p. 1-p. 7.

\* cited by examiner

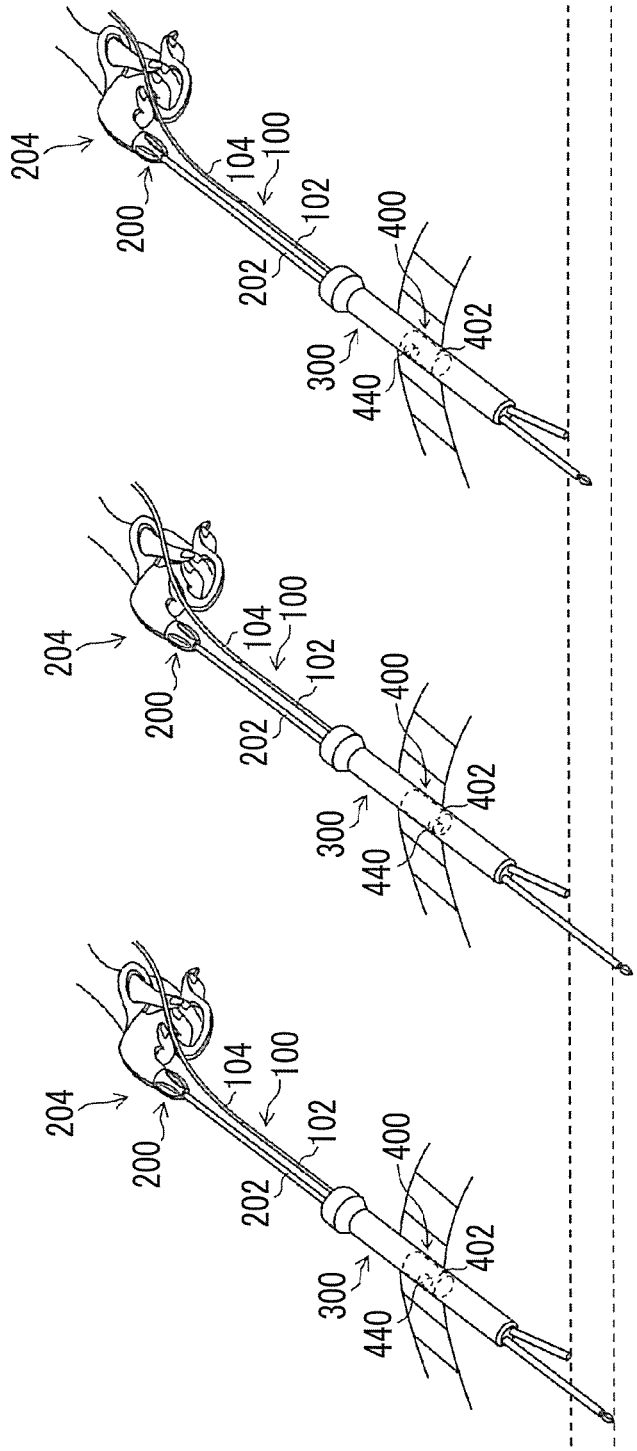

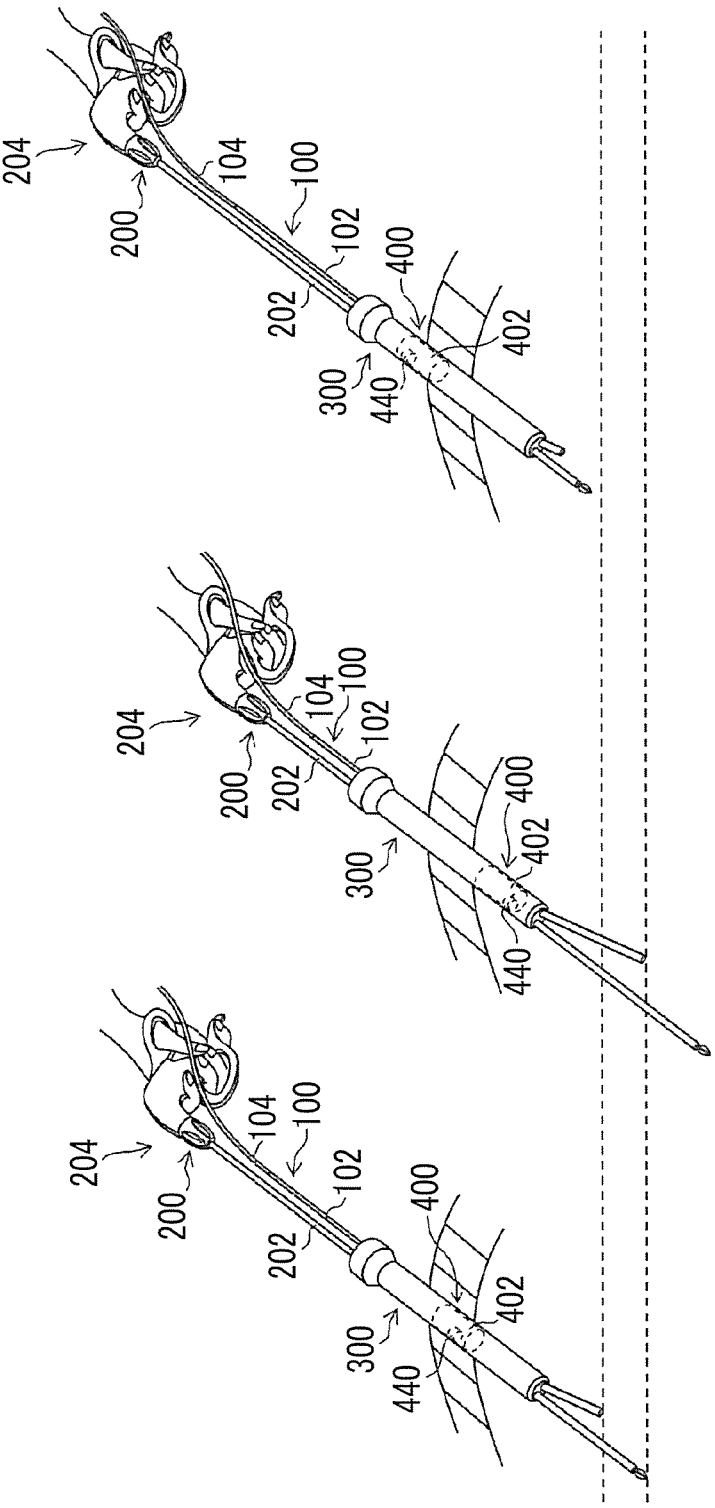

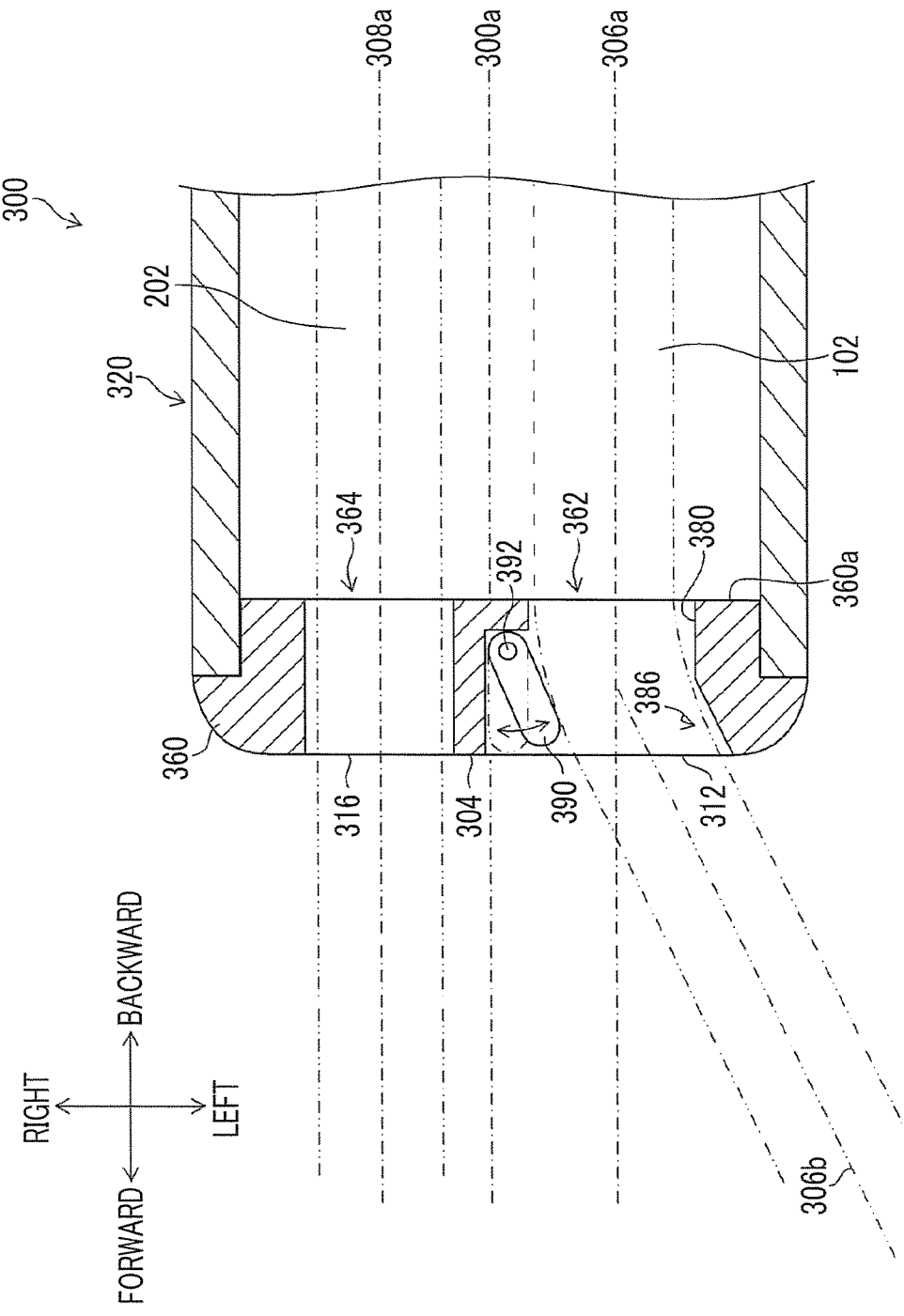

ENDOSCOPIC SURGICAL DEVICE AND OVERTUBE

CROSS-REFERENCE TO RELATED APPLICATIONS

This application is a Continuation of PCT International Application No. PCT/JP2015/059352 filed on Mar. 26, 2015, which claims priority under 35 U.S.C. § 119(a) to U.S. Provisional Application No. 61/971,222 filed on Mar. 27, 2014. Each of the above applications is hereby expressly incorporated by reference, in their entirety, into the present application.

BACKGROUND OF THE INVENTION

1. Field of the Invention

The present invention relates to an endoscopic surgical device and an overtube, and particularly, relates to an endoscopic surgical device and an overtube that can operate an endoscope and a treatment tool inserted through two insertion passages provided in the overtube in an interlocking manner.

2. Description of the Related Art

In recent years, since invasion to a patient is small compared to surgery in which a laparotomy, a thoracotomy, or the like, is performed, endoscopic surgery using endoscopes (hard endoscopes), such as a laparoscope, has been widely performed. In endoscopic surgery, a plurality of holes are made in a patient's body wall, an endoscope is inserted into a body cavity from one hole of these, and a treatment tool is inserted into the body cavity from another hole. Then, treatment of a living body tissue is performed with the treatment tool while observing the living body tissue within the body cavity with the endoscope.

Generally, in endoscopic surgery, one or a plurality of treatment tools are used simultaneously with the endoscope. Therefore, since it is difficult for one surgeon to simultaneously operate the endoscope and the plurality of treatment tools, for example, a task, such as operating a treatment tool that the surgeon holds with his/her both hands while making an assistant called an endoscopic technician operate the endoscope is normally performed.

In this way, in endoscopic surgery, it is usual that the surgeon's hands are occupied by the operation of the treatment tool, and the operation of the endoscope is performed by the assistant. Therefore, in a case where the observation position of the endoscope is changed, the surgeon needs to give sequential instructions to the assistant. Hence, the task of correctly directing the orientation of the endoscope to a direction desired by the surgeon is difficult, and stress is likely to be imposed on the surgeon. Additionally, since the assistant performs an operation after the surgeon issues an instruction, there is a tendency that surgery time is likely to be prolonged. Additionally, the assistant needs to operate the endoscope so as not to interfere with a surgeon's procedure, and the operation is likely to become complicated.

In contrast, the present applicant suggests the following technique. In this technique, an overtube that guides an insertion part of an endoscope and an insertion part of a treatment tool into a body cavity includes a tubular overtube body that is inserted in a state where the insertion part of the endoscope and the insertion part of the treatment tool are made to be parallel to each other, a movable body that is movable in an axial direction and has an endoscope holding part and a treatment tool holding part is provided inside the overtube body, the insertion part of the endoscope and the insertion part of the treatment tool are held by the respective holding parts in a state where the insertion parts are made to be parallel to each other, and if the insertion part of the treatment tool is moved in the axial direction, the insertion part of the endoscope also moves in the axial direction in an interlocking manner with this movement (refer to WO2013/176167A). According to this technique, the number of holes made in the patient's body wall can be reduced, the invasion to a patient can be reduced, and the visual field of the endoscope can be easily changed while the surgeon operates the treatment tool without asking for an assistant's help.

Meanwhile, in an overtube (trocar sleeve) disclosed in JP2011-224376A, a shaft-shaped central portion of an endoscope with a high rigidity, and a shaft portion of a treatment tool are inserted in the state where these portions are made to be parallel to each other. However, in order to prevent interference between the endoscope and the treatment tool inside and outside a body cavity, an operating portion connected to a proximal side of the shaft-shaped central portion of the endoscope and a distal end portion connected to a distal side (body cavity side) are arranged so as to be offset or inclined with respect to a longitudinal axis of the shaft-shaped central portion.

Additionally, JP1998-94513A (JP-H10-94513A) discloses a configuration in which, in an endoscopic surgical device having a tubular member (tube shaft) including an optical system and a work passage, an inclined part having a guide groove is provided inside the tubular member, and a distal end of the optical system is bent toward a treatment tool (work tool) inserted through the work passage by the guide groove of the inclined part so that a work area of the treatment tool can be observed by the optical system.

SUMMARY OF THE INVENTION

Meanwhile, in the technique that the present applicant suggested previously, the insertion part of the endoscope and the insertion part of the treatment tool are inserted through the overtube in a state where these insertion parts are made parallel to each other. However if these insertion parts are excessively brought close to each other, the line of sight of the endoscope and the forward and backward movement directions of the treatment tool substantially coincide with each other. In this case, when the treatment tool approaches the living body tissue within the body cavity, dead areas may be generated by portions other than the distal end of the treatment tool, so that the state of the distal end of the treatment tool cannot be checked. For this reason, if the insertion part of the endoscope and the insertion part of the treatment tool are kept away from each other (that is, if these insertion parts are offset from each other in a direction away from that of the parallel state) in order to secure the visual field of the endoscope, there is a problem that the external diameter of the overtube may become large, and invasiveness to a patient may become large. For this reason, it is desired to secure the visual field of the endoscope without increasing the external diameter of the overtube.

Meanwhile, in the technique disclosed in JP2011-224376A, there are problems that it is necessary to use a special endoscope having an operating portion and a distal side (body cavity side) that is offset or obliquely arranged with respect to a longitudinal axis of a shaft-shaped central portion, versatility may be insufficient, and an increase in cost may be caused.

Additionally, in the technique disclosed in JP1998-94513A (JP-H10-94513A), a structure in which the distal end of the optical system is bent in a direction approaching the treatment tool by the inclined groove provided inside the tubular member is adopted. However, in this structure, the optical system and the treatment tool cannot be brought sufficiently close to each other, and there is a limit to a reduction in the diameter of the tubular member.

The invention has been made in view of such circumstances, and an object thereof is to provide an endoscopic surgical device and an overtube that allows the state of a distal end of a second medical instrument to be easily checked while reducing the diameter of the overtube, and can improve surgical efficiency, in a configuration in which a first medical instrument (for example, an endoscope) is made to be movable forward and backward in an interlocking manner with the forward and backward movement of the second medical instrument (for example, a treatment tool).

In order to achieve the above object, an endoscopic surgical device related to an aspect of the invention is an endoscopic surgical device including a first medical instrument having a first insertion part to be inserted into a body cavity; a second medical instrument having a second insertion part to be inserted into the body cavity; and an overtube that guides the first insertion part and the second insertion part into the body cavity. The overtube includes an overtube body that passes through a body wall and is inserted into the body cavity, a first insertion passage that is provided inside the overtube body and allows the first insertion part to be inserted therethrough so as to be movable forward and backward, a second insertion passage that is provided inside the overtube body and allows the second insertion part to be inserted therethrough so as to be movable forward and backward, and an interlocking member that includes a first coupling part coupled to the first insertion part inserted through the first insertion passage and a second coupling part coupled to the second insertion part inserted through the second insertion passage, the interlocking member being arranged inside the overtube body so as to be movable forward and backward. The interlocking member has a dead zone where forward and backward movement of either the first insertion part or the second insertion part does not interlock with the movement of the other and a sensing zone where the forward and backward movement of either the first insertion part or the second insertion part interlocks with the movement of the other. The first insertion passage is provided with a guide part that guides a distal end of the first insertion part in a direction away from a distal end of the second insertion part when the first insertion part is moved toward a distal end side thereof.

According to this aspect, the distal end of the first insertion part of the first medical instrument is guided in the direction away from the distal end of the second insertion part of the second medical instrument by the guide part provided in the first insertion passage. Accordingly, when the second medical instrument approaches a living body tissue within the body cavity, dead areas are not easily generated by portions other than the distal end of the second medical instrument. Therefore, the state of the distal end of the second medical instrument can easily be checked while reducing the diameter of the overtube, and surgical efficiency can be improved, in a configuration in which the first medical instrument is made to be movable forward and backward in an interlocking manner with the forward and backward movement of the second medical instrument.

In the endoscopic surgical device related to the aspect of the invention, an aspect is preferable in which the first medical instrument is an endoscope in which an observation part is provided at the distal end of the first insertion part, and the second medical instrument is a treatment tool in which a treatment part is provided at the distal end of the second insertion part.

In the endoscopic surgical device related to the aspect of the invention, an aspect is preferable in which the guide part includes an inclined part that is provided to protrude toward the inside of the first insertion passage, and the inclined part includes a guide surface that guides a delivery direction of the distal end of the first insertion part delivered from the first insertion passage in an oblique direction away from the second insertion passage.

In the endoscopic surgical device related to the aspect of the invention, an aspect is preferable in which the guide part includes a movable guide part that allows a delivery direction of the distal end of the first insertion part delivered from the first insertion passage to be variable between a straight-ahead direction parallel to the second insertion passage and an oblique direction away from the second insertion passage.

In the endoscopic surgical device related to the aspect of the invention, an aspect is preferable in which at least a portion of the first insertion part delivered into the body cavity from the distal end of the first insertion passage has flexibility.

Additionally, in the endoscopic surgical device related to the aspect of the invention, an aspect is preferable in which the portion delivered into the body cavity has elasticity.

An overtube related to another aspect of the invention is an overtube used in an endoscopic surgical device including a first medical instrument having a first insertion part to be inserted into a body cavity, a second medical instrument having a second insertion part to be inserted into the body cavity, and the overtube that guides the first insertion part and the second insertion part into the body cavity. The overtube includes an overtube body that passes through a body wall and is inserted into the body cavity; a first insertion passage that is provided inside the overtube body and allows the first insertion part to be inserted therethrough so as to be movable forward and backward; a second insertion passage that is provided inside the overtube body and allows the second insertion part to be inserted therethrough so as to be movable forward and backward; and an interlocking member that includes a first coupling part coupled to the first insertion part inserted through the first insertion passage and a second coupling part coupled to the second insertion part inserted through the second insertion passage, the interlocking member being arranged inside the overtube body so as to be movable forward and backward. The interlocking member has a dead zone where forward and backward movement of either the first insertion part or the second insertion part does not interlock with the movement of the other and a sensing zone where the forward and backward movement of either the first insertion part or the second insertion part interlocks with the movement of the other. The first insertion passage is provided with a guide part that guides a distal end of the first insertion part in a direction away from a distal end of the second insertion part when the first insertion part is moved toward a distal end side thereof.

According to the invention, the state of the distal end of the treatment tool can easily be checked while reducing the diameter of the overtube, and surgical efficiency can be improved, in a configuration in which the endoscope is made to be movable forward and backward in an interlocking manner with the forward and backward movement of the treatment tool.

BRIEF DESCRIPTION OF THE DRAWINGS

FIGS. 15A to 15C are views illustrating an aspect of the operation when only a treatment tool moves forward and backward.

FIGS. 16A to 16C are views illustrating an aspect of the operation when the endoscope moves forward and backward in an interlocking manner with the treatment tool through an interlocking function of the slider.

FIG. 17 is a sectional view of another embodiment of a guide part in the distal end cap of the overtube.

DESCRIPTION OF THE PREFERRED EMBODIMENTS

Preferred embodiments of the invention will be described below in detail according to the accompanying drawings. In addition, any of the drawings may illustrate main parts in an exaggerated manner for description, and may have dimensions different from actual dimensions.

Figure 1:
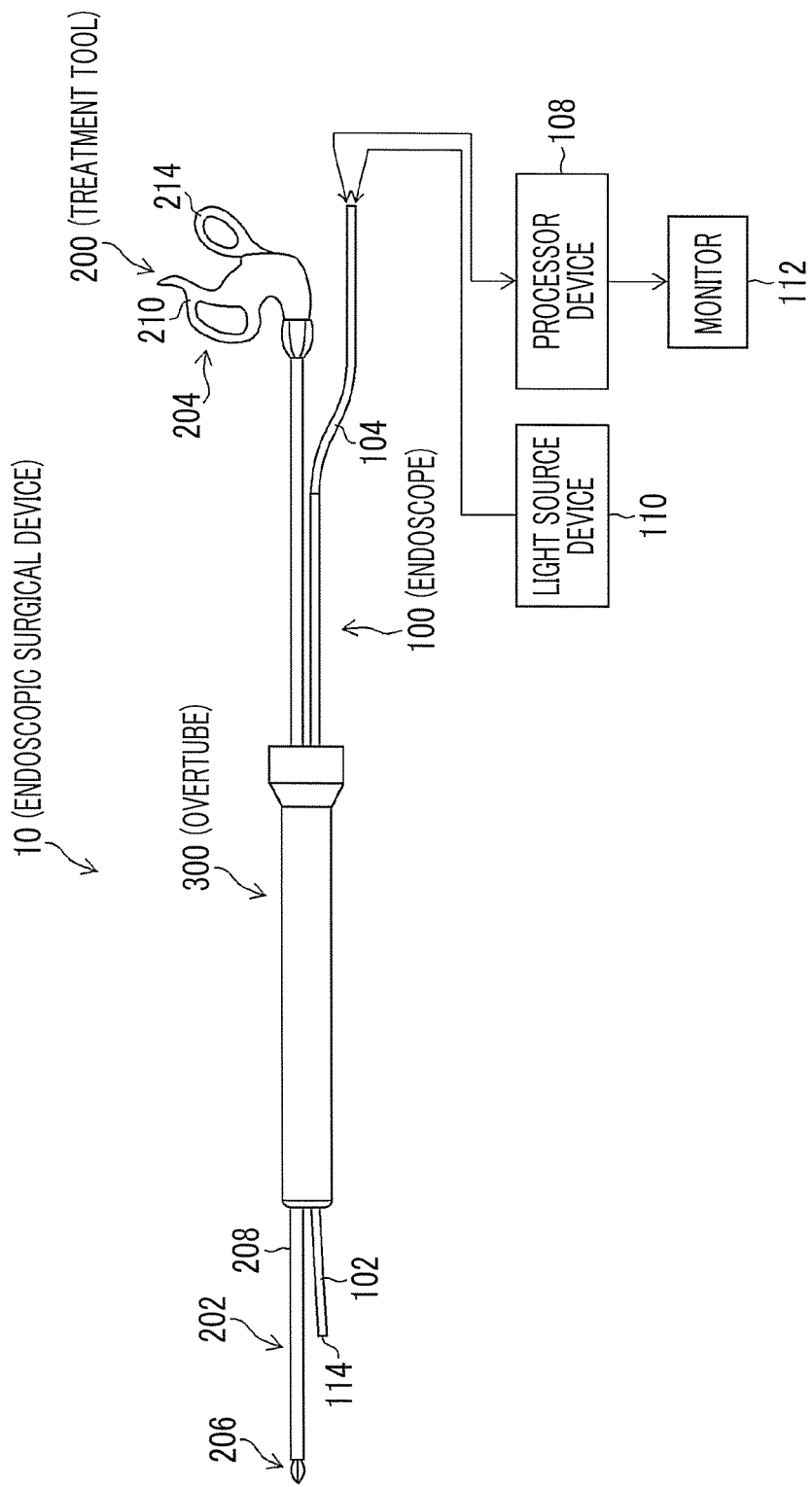
FIG. 1 is a schematic block diagram of an endoscopic surgical device related to the invention.

FIG. 1 is a schematic block diagram of an endoscopic surgical device related to the invention. As illustrated in FIG. 1, an endoscopic surgical device 10 includes an endoscope 100 that observes the inside of a patient's body cavity, a treatment tool 200 for examining or treating a diseased site within the patient's body cavity, and an overtube 300 that is inserted into a body wall and guides the endoscope 100 and the treatment tool 200 into the body cavity. In addition, the endoscope 100 is equivalent to a first medical instrument, and the treatment tool 200 is equivalent to a second medical instrument.

The endoscope 100 is, for example, a hard endoscope, such as a laparoscope, and includes an insertion part 102 (hereinafter referred to as "endoscope insertion part") that is inserted into a body cavity and has an outer peripheral part surrounded by an elongated hard tubular body, and a cable part 104 that is provided continuously with a base end side of the endoscope insertion part 102 and that has an outer peripheral part surrounded by an elongated flexible tubular body. However, an endoscope in which the tubular body of the outer peripheral part of the endoscope insertion part 102 is formed of an elastic body, such as a nickel titanium (NiTi) alloy and the endoscope insertion part 102 is bendable is used as the endoscope 100. In addition, the endoscope insertion part 102 is equivalent to a first insertion part.

The cable part 104 indicates a flexible cable portion in which a wire rod, such as a cable or a light guide, which extends from a base end of the endoscope insertion part 102, is housed by covering the wire rod with, for example, a flexible insulating member, such as polyvinyl chloride.

A connector (not illustrated) is provided at an end of the cable part 104 on its extension destination, and each of a processor device 108 and a light source device 110 is detachably connected to the cable part via the connector. Additionally, the processor device 108 is connected to a monitor 112 via a cable.

Figure 2:
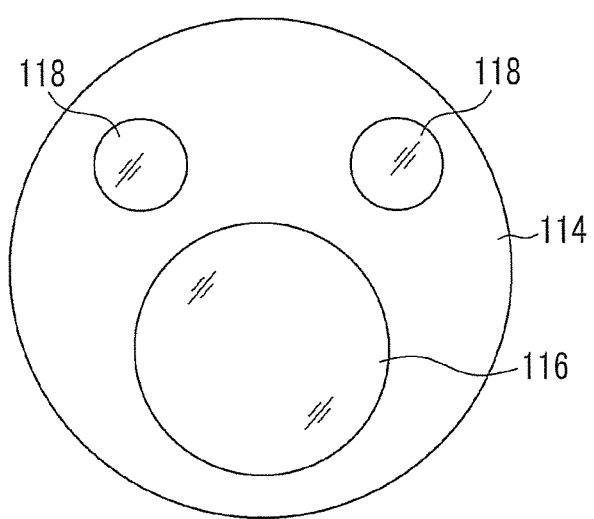
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

The observation window 116 is a constituent element of an observation part of the endoscope 100, and an objective lens of an observation optical system, and an image pick-up element, such as a charge coupled device (CCD) or a complementary metal oxide semiconductor (CMOS), which is arranged at an image pick-up position of the objective lens, are disposed behind the observation window 116. A signal cable (not illustrated) connected to a substrate that supports this image pickup element is inserted through the endoscope insertion part 102 and the cable part 104 of FIG. 1, is provided to extend up to the connector (not illustrated), and is connected to the processor device 108. An observation image picked up from the observation window 116 is formed on a light-receiving surface of the image pick-up element, and is converted into electrical signals (image pick-up signals), and the electrical signals are output to the processor device 108 via the signal cable and are converted into video signals. Then, the video signals are output to the monitor 112 connected to the processor device 108, and the observation image (endoscope image) is displayed on a screen of the monitor 112.

An exit end of the light guide (not illustrated) is disposed behind the illumination windows 118 and 118 of FIG. 2. The light guide is inserted through the endoscope insertion part 102 and the cable part 104 of FIG. 1 and has an incident end disposed within the connector (not illustrated). Therefore, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of illumination windows 118 is not limited, and the number thereof may be one or may be three or more. Additionally, the endoscope 100 may not include the light guide.

As illustrated in FIG. 1, the treatment tool 200 consists of, for example, forceps, and includes an elongated insertion part 202 (hereinafter referred to as a "treatment tool insertion part") that is inserted into a body cavity, an operating part 204 that is provided on the base end side of the treatment tool insertion part 202 and is gripped by a surgeon, and a treatment part 206 that is provided on a distal end side of the treatment tool insertion part 202 and is operable by the operation of the operating part 204. In addition, the treatment tool insertion part 202 is equivalent to a second insertion part.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is turnably coupled to the fixed handle 210 via a turning pin. A base end of the operating shaft is coupled to the movable handle 214.

The treatment part 206 is provided with a pair of gripping members that is openable and closable. The gripping members are coupled to a distal end of the operating shaft via a driving mechanism (not illustrated). With the turning operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, and an ultrasonic aspirator.

As illustrated in FIG. 1, the overtube 300 allows the endoscope insertion part 102 and the treatment tool insertion part 202, which are inserted thereinto from the base end side, to be inserted therethrough and delivered from the distal end side. By inserting the overtube 300 into a body wall and having a distal end side thereof arranged outside of the body and a base end side thereof arranged within the body cavity, it is possible to guide the endoscope insertion part 102 and the treatment tool insertion part 202 into the body cavity with one overtube 300. Additionally, the overtube 300 includes an interlocking function of interlocking the endoscope insertion part 102 with the treatment tool insertion part 202 to move these insertion parts forward and backward as will be described below in detail. For example, the endoscope insertion part 102 can also be moved forward and backward by the forward and backward movement operation of only the treatment tool insertion part 202, and a suitable observation image can be obtained without performing the forward and backward movement operation of the endoscope insertion part 102.

Moreover, the overtube 300 guides a distal end of the endoscope insertion part in a direction away from a distal end of the treatment tool insertion part 202 inserted through the overtube 300 when the endoscope insertion part 102 inserted through the overtube 300 is moved toward the distal end side. That is, the overtube 300 bends the endoscope insertion part 102 at a distal end thereof, and delivers the endoscope insertion part 102 in the direction away from the treatment tool insertion part 202. Accordingly, a distal end of the treatment part 206 can be visually recognized on an observation image by widening the spacing between the observation part (observation window 116) at the distal end of the endoscope insertion part 102 and the treatment part 206 of the treatment tool insertion part 202 so that a distal end portion of the treatment part 206 of the treatment tool insertion part 202 does not become a dead area. The detailed description will be made below.

Figure 3:
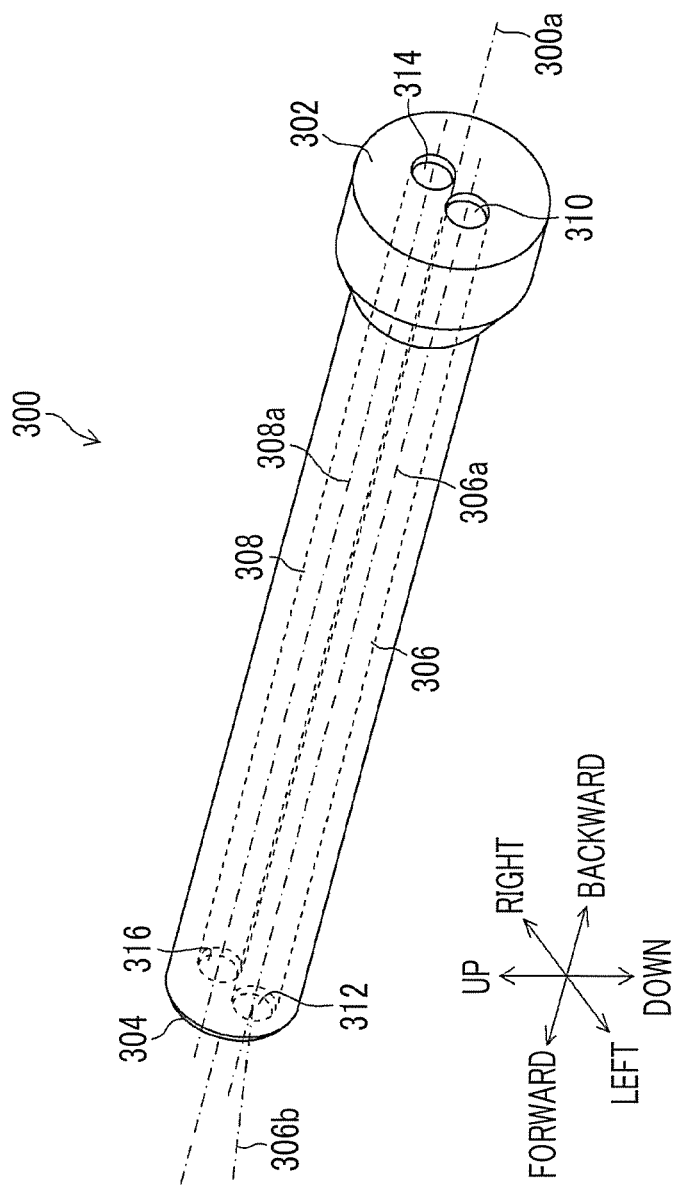
FIG. 3 is an external perspective view illustrating an overtube.

FIG. 3 is an external perspective view illustrating the overtube 300.

As illustrated in this drawing, the overtube 300 has an elongated columnar shape as a whole, and has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward. These insertion passages are parallel to a reference axis 300a (longitudinal axis) indicating a central axis of the overtube.

If a central axis of the endoscope insertion passage 306 is referred to as an endoscope insertion axis 306a and a central axis of the treatment tool insertion passage 308 is referred to as a treatment tool insertion axis 308a, the endoscope insertion axis 306a and the treatment tool insertion axis 308a are parallel to each other, and is also parallel to the reference axis 300a. The endoscope insertion axes 306a and the treatment tool insertion axes 308a are equivalent to positions of the central axes of the endoscope insertion part 102 and the treatment tool insertion part 202 that are respectively inserted through the endoscope insertion passage 306 and the treatment tool insertion passage 308. Additionally, in the present embodiment, the reference axis 300a, the endoscope insertion axis 306a, and the treatment tool insertion axis 308a are arranged on the same plane. However, a configuration in which the reference axis 300a, the endoscope insertion axis 306a, and the treatment tool insertion axis 308a are arranged on the same plane may not be adopted.

In addition, regarding the position and orientation of a space where the overtube 300 has been arranged, terms called forward, backward, left, right, up, and down are used with the orientation from the base end surface 302 in a direction along the reference axis 300a to the distal end surface 304 defined as the forward and with the orientation from the reference axis 300a to the endoscope insertion axis 306a defined as the left.

The base end surface 302 of the overtube 300 is provided with an endoscope insertion port 310 that allows the endoscope insertion part 102 to be inserted into the endoscope insertion passage 306 therethrough, and a treatment tool insertion port 314 that allows the treatment tool insertion part 202 to be inserted into the treatment tool insertion passage 308 therethrough.

The distal end surface 304 of the overtube 300 is provided with an endoscope delivery port 312 that allows the endoscope insertion part 102 inserted into the endoscope insertion passage 306 to be delivered to the outside therethrough, and a treatment tool delivery port 316 that allows the treatment tool insertion part 202 inserted into the treatment tool insertion passage 308 to be delivered to the outside therethrough.

Additionally, a guide part is provided in the vicinity of the endoscope delivery port 312 to guide the endoscope insertion part 102 inserted through the endoscope insertion passage 306 and delivered from the endoscope delivery port 312 in a direction in which the distal end of the endoscope insertion part is away from the treatment tool insertion part 202 inserted through the treatment tool insertion passage 308. Accordingly, the endoscope insertion part 102 delivered from the endoscope delivery port 312 is arranged at a position along an endoscope delivery axis 306b with the endoscope delivery axis 306b illustrated in FIG. 3 as a delivery direction. The endoscope delivery axis 306b is equivalent to the position of a central axis of the endoscope insertion part 102 delivered from the endoscope delivery port 312. The endoscope delivery axis 306b intersects the endoscope insertion axis 306a in the vicinity of the endoscope delivery port 312, and extends toward an oblique front left side from a position of intersection with the endoscope insertion axis 306a on a plane including the endoscope insertion axis 306a and the treatment tool insertion axis 308a.

Figure 4:
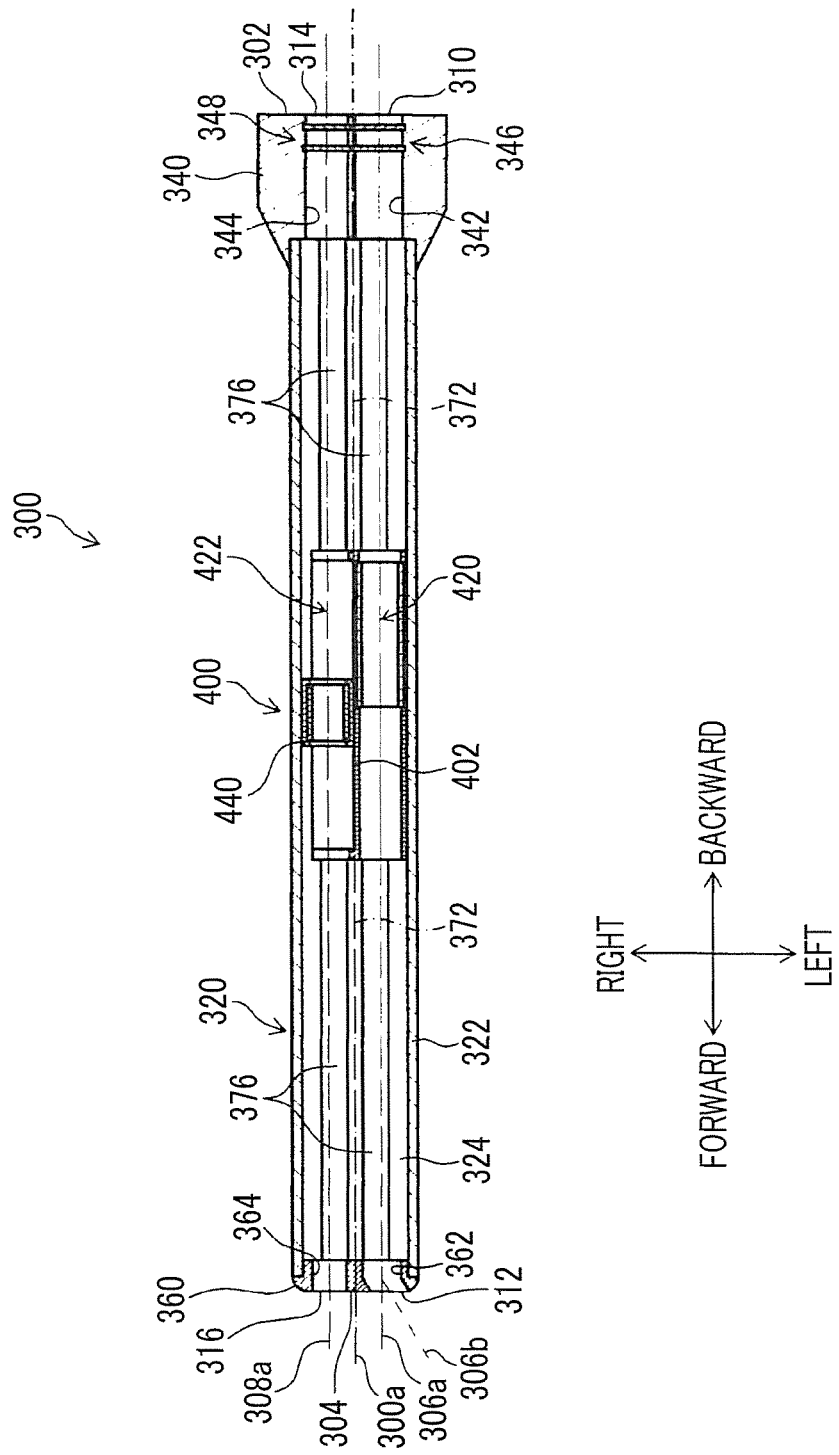
FIG. 4 is a sectional view illustrating the internal structure of the overtube.

FIG. 4 is a sectional view illustrating the internal structure of the overtube 300, and illustrates a section cut in a plane that includes the reference axis 300a and is orthogonal to an upward-downward direction.

As illustrated in this drawing, the overtube 300 has an overtube body 320 that occupies substantially the entire area in the forward-backward direction, a base end cap 340 that is attached to a rear end (base end) of the overtube 300, a distal end cap 360 that is attached to a distal end, and a slider 400 (the slider 400 is one form of an interlocking member) that is arranged inside the overtube 300.

In addition, the base end cap 340 and the distal end cap 360 are some of the constituent elements of the overtube body of the invention, and may be formed separately from or formed integrally with the overtube body 320.

The overtube body 320 is formed in an elongated cylindrical shape having the reference axis 300a as a central axis using hard resins, metals, or the like, and has an outer wall 322 that surrounds an outer periphery, and a cavity part 324 that penetrates from a base end of the overtube body 320 to a distal end thereof.

The cavity part 324 includes spaces serving as the endoscope insertion passage 306 and the treatment tool insertion passage 308, and houses the slider 400 and the like.

The base end cap 340 is formed in a columnar shape of which the diameter is made larger than the external diameter of the overtube body 320 using hard resins, metals, or the like, and a rear end surface thereof constitutes the base end surface 302 of the overtube 300. The base end cap 340 is provided with a through-hole 342 and a through-hole 344 that form a portion of the endoscope insertion passage 306 and a portion of the treatment tool insertion passage 308, respectively. In the base end surface 302, an opening of the through-hole 342 is equivalent to the above-described endoscope insertion port 310, and an opening of the through-hole 344 is equivalent to the above-described treatment tool insertion port 314.

Additionally, the through-holes 342 and 344 are provided with valve members 346 and 348. The valve members 346 and 348, for example, open in a case where the endoscope insertion part 102 and the treatment tool insertion part 202 are inserted therethrough and come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

The distal end cap 360 is formed of hard resins, metals, or the like, and a front end surface thereof constitutes the distal end surface 304 of the overtube 300. The distal end cap 360 is provided with a through-hole 362 and a through-hole 364 that form a portion of the endoscope insertion passage 306 and a portion of the treatment tool insertion passage 308, respectively. In the distal end surface 304, an opening of the through-hole 362 is equivalent to the above-described endoscope delivery port 312, and an opening of the through-hole 364 is equivalent to the treatment tool delivery port 316.

Figure 5:
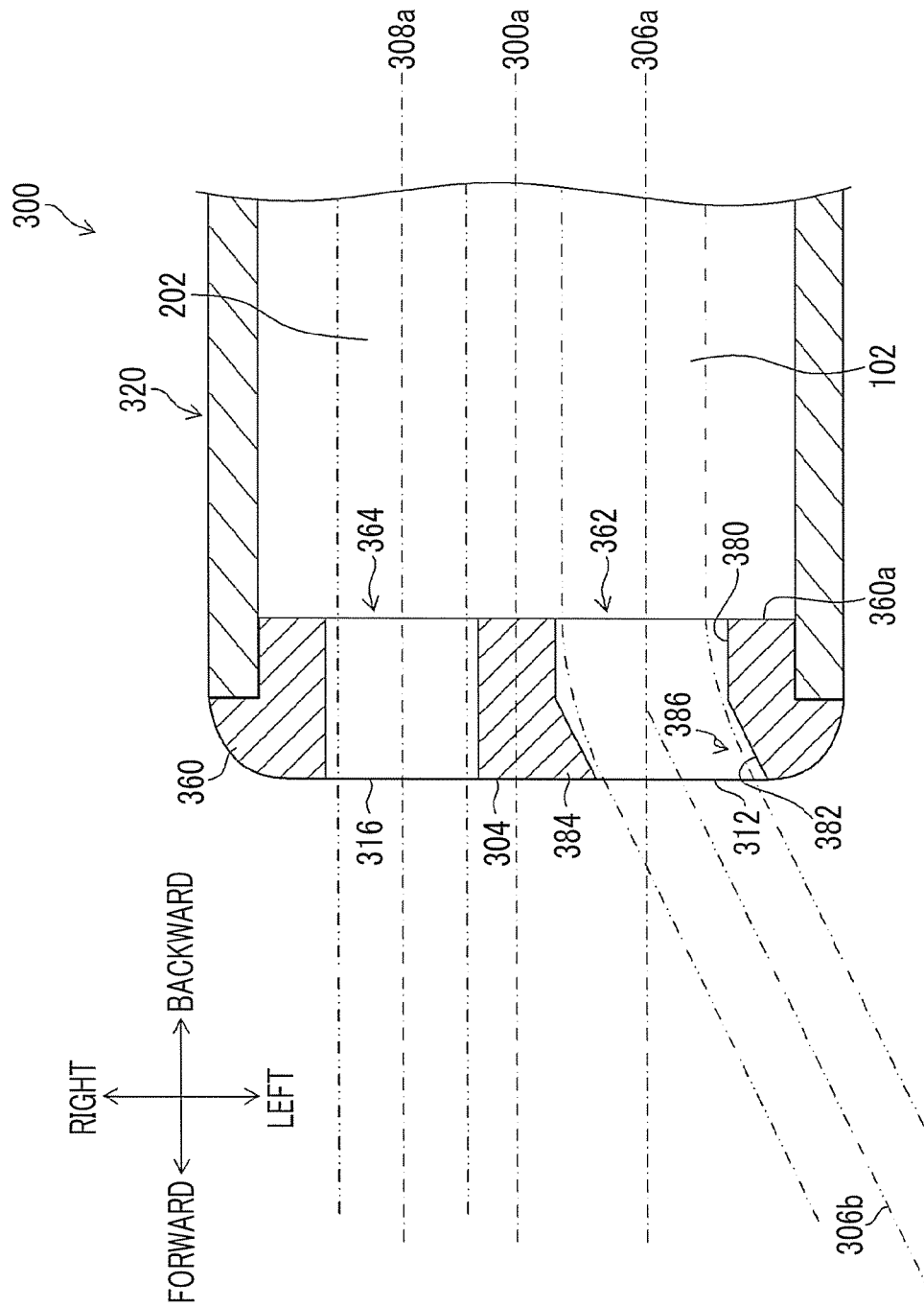
FIG. 5 is an enlarged sectional view illustrating a portion of a distal end cap of the overtube.

FIG. 5 is an enlarged sectional view illustrating a portion of the distal end cap 360 of the overtube 300. As illustrated in this drawing, the through-hole 364 that forms a portion of the treatment tool insertion passage 308 is formed in a columnar shape with the treatment tool insertion axis 308a as a central axis, and has a diameter with a size such that the treatment tool insertion part 202 is insertable therethrough. The treatment tool insertion part 202 inserted into the treatment tool insertion passage 308 from the treatment tool insertion port 314 in the base end surface 302 of the overtube 300 is inserted with the position of the treatment tool insertion axis 308a as a position of a central axis within the overtube body 320 by coupling with the slider 400 to be described below, or the like, is inserted through the through-hole 364, and is delivered from the treatment tool delivery port 316 with the direction of the treatment tool insertion axis 308a as a delivery direction thereof. Then, the treatment tool insertion part 202 delivered from the treatment tool delivery port 316 is arranged with the position of the treatment tool insertion axis 308a as the position of the central axis thereof.

Meanwhile, the through-hole 362 that forms a portion of the endoscope insertion passage 306 is formed from a rear straight hole 380 and a front guide hole 382.

The straight hole 380 is formed in a columnar shape with the endoscope insertion axis 306a as a central axis, in a range from the position of a rear end surface 360a of the distal end cap 360 to a position (for example, a substantially central position of the width of the distal end cap 360 in the forward-backward direction) closer to the rear side than the front end surface (distal end surface 304), and has a diameter with a size such that the endoscope insertion part 102 is insertable therethrough.

The guide hole 382 is formed so that an inner wall surface thereof is inclined toward an oblique front left side, while communicate with a front end of the straight hole 380 with the endoscope delivery axis 306b as a central axis, in a range from the position of the front end of the straight hole 380 to the position of the distal end surface 304 of the distal end cap 360 and maintaining the hole shape (circular shape) of the front end of the straight hole 380. The endoscope delivery axis 306b extends toward the oblique front left side from the position of intersection with the endoscope insertion axis 306a on the plane including the endoscope insertion axis 306a and the treatment tool insertion axis 308a, as described above.

Although the guide hole 382 has an elliptical shape in a shape orthogonal to the endoscope delivery axis 306b, the length of a minor axis thereof has a size such that the endoscope insertion part 102 is insertable through the guide hole, and the guide hole 382 is formed with a size such that the endoscope insertion part 102 is insertable therethrough. In addition, an opening of the front end of the guide hole 382 becomes the endoscope delivery port 312.

A right wall portion of the guide hole 382, which protrudes further toward a left side than a wall surface of the straight hole 380, is an inclined part that has an inclined guide surface, and acts as a guide part 384 that guides the endoscope insertion part 102 in the direction of the endoscope delivery axis 306b. The guide part 384 protrudes to a position where the guide part interferes with (abuts against) the endoscope insertion part 102 inserted through the overtube body 320, with at least the position of the endoscope insertion axis 306a as a position of a central axis thereof.

In addition, the amount of protrusion of the guide part 384 to the left side can be set to a suitable magnitude depending to the length, in the forward-backward direction, of the guide hole 382 formed in the distal end cap 360, if the inclination angle of the endoscope delivery axis 306b with respect to the endoscope insertion axis 306a is fixed to a predetermined angle.

Additionally, a left wall portion of the guide hole 382, which is cut out further toward the left side than the wall surface of the straight hole 380 acts as a cutout part 386 for avoiding any interference with the endoscope insertion part 102 bent by the guide part 384.

According to such a through-hole 362, the endoscope insertion part 102 inserted into the endoscope insertion passage 306 from the endoscope insertion port 310 in the base end surface 302 of the overtube 300 is inserted with the position of the endoscope insertion axis 306a as a position of a central axis within the overtube body 320 by coupling with the slider 400 to be described below, or the like, and is inserted through the through-hole 362. In this case, the endoscope insertion part 102 abuts against the guide part 384 of the guide hole 382 within the through-hole 362, is bent leftward, and is guided in the direction of the wall surface of the guide part 384, that is, in the direction of the endoscope delivery axis 306b. The endoscope insertion part 102 delivered from the endoscope delivery port 312 with the direction of the endoscope delivery axis 306b as a delivery direction is arranged with the position of the endoscope delivery axis 306b as a position of a central axis.

In addition, the bending of the endoscope insertion part 102 may not occur locally at the position of the rear end of the guide hole 382 as illustrated in FIG. 5, or may occur over a wide range of the endoscope insertion part 102 by abutting against the guide part 384. Additionally, the direction of the central axis of the guide hole 382, that is, the direction of the wall surface of the guide part 384, and the direction of the endoscope delivery axis 306b that is the delivery direction of the endoscope insertion part 102 may not necessarily coincide with each other, and the guide part 384 just has to a guide surface with an arbitrary shape that comes into contact with the endoscope insertion part 102 so that the direction of the endoscope delivery axis 306b becomes a desired direction.

According to the configuration of the overtubes 300 as above, when the endoscope insertion part 102 inserted through the endoscope insertion passage 306 is moved toward the distal end side, the distal end of the endoscope insertion part 102 is guided by the guide part 384 in the direction away from the distal end (treatment part 206) of the treatment tool insertion part 202 inserted through the treatment tool insertion passage 308. That is, the position of the distal end (distal end surface 114) of the endoscope insertion part 102 inserted through the endoscope insertion passage 306 and delivered from the endoscope delivery port 312 has a greater separation distance in a radial direction with respect to the treatment tool insertion part 202 (treatment tool insertion axis 308a) inserted through the treatment tool insertion passage 308, as the amount of protrusion from the endoscope delivery port 312 becomes larger.

Figure 6:
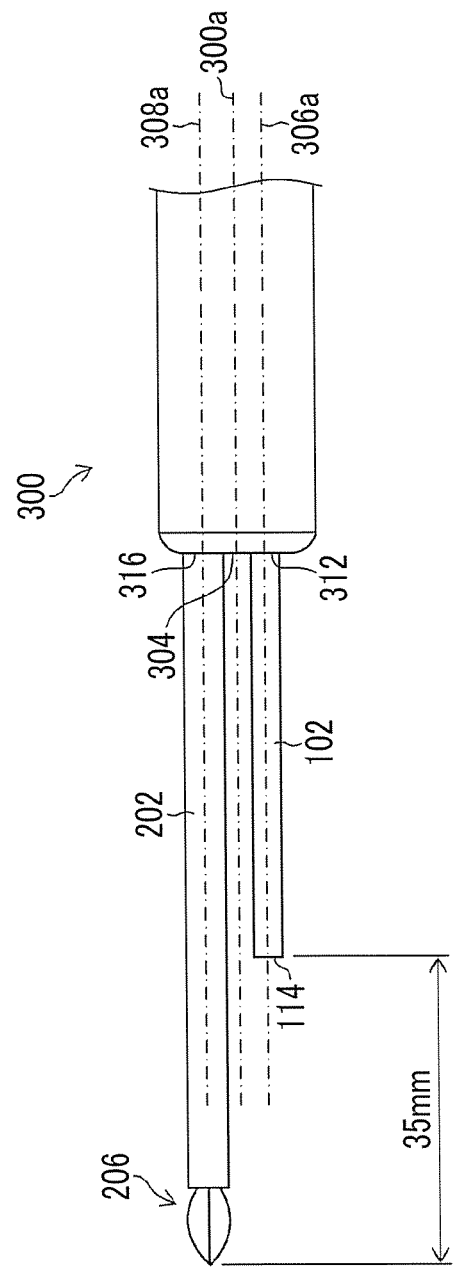
FIG. 6 is a view illustrating an aspect of the endoscope insertion part and a treatment tool insertion part that are delivered in parallel from the overtube.

Here, in a case where the endoscope insertion part 102 and the treatment tool insertion part 202 are respectively delivered in directions parallel to each other, from the endoscope delivery port 312 and the treatment tool delivery port 316 of the overtube 300, the endoscope insertion part 102 and the treatment tool insertion part 202 approach each other, as illustrated in FIG. 6, with a reduction in the diameter of the overtube 300.

Figure 7:
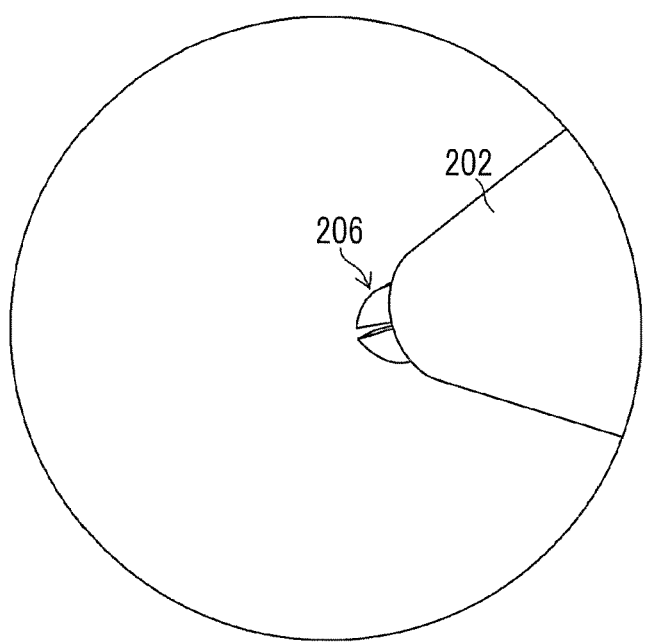
FIG. 7 is a view illustrating an observation image obtained in the state of FIG. 6.

Therefore, even if the amount of protrusion of the treatment tool insertion part 202 from the treatment tool delivery port 316 and the amount of protrusion of the endoscope insertion part 102 from the endoscope delivery port 312 are adjusted (for example, a state where the amount of protrusion of the treatment tool insertion part 202 is 35 mm greater than the amount of protrusion of the endoscope insertion part 102) so that the treatment part 206 at the distal end of the treatment tool insertion part 202 is reflected within a visual field range of the observation part provided at the distal end of the endoscope insertion part 102, there is a concern that dead areas may be generated by portions other than the distal end of the treatment part 206, and a situation where the state of the distal end of the treatment part 206 cannot be checked may occur, as in an observation image illustrated in FIG. 7.

Figure 8:
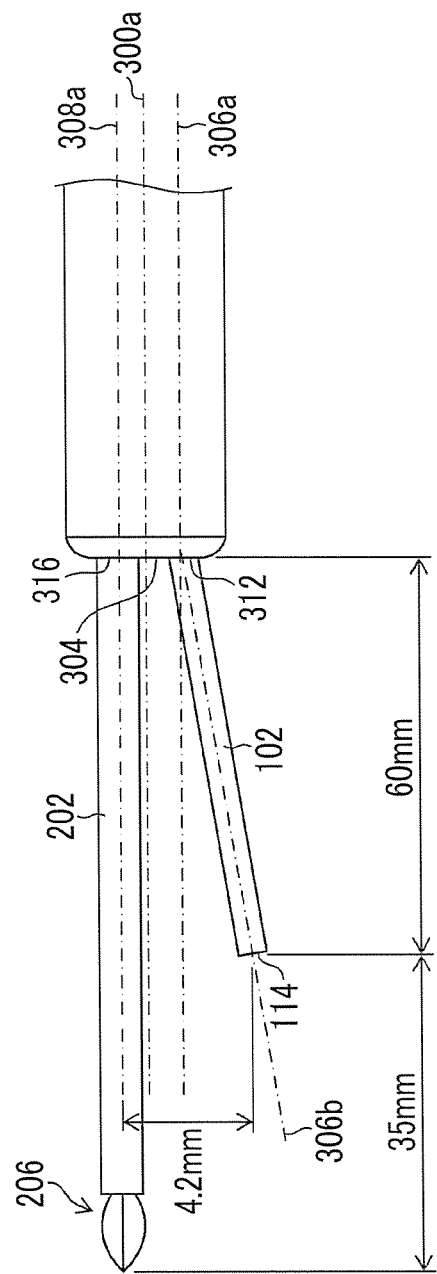
FIG. 8 is a view illustrating an aspect of the endoscope insertion part and the treatment tool insertion part that are delivered from the overtube of the present embodiment.

Meanwhile, in a case where the endoscope insertion part 102 inserted through the endoscope insertion passage 306 like the overtube 300 of the present embodiment is delivered obliquely with respect to the treatment tool insertion part 202 inserted through the treatment tool insertion passage 308, the endoscope insertion part 102 and the treatment tool insertion part 202 that are respectively delivered from the endoscope delivery port 312 and the treatment tool delivery port 316 can be separated from each other as illustrated in FIG. 8.

Figure 9:
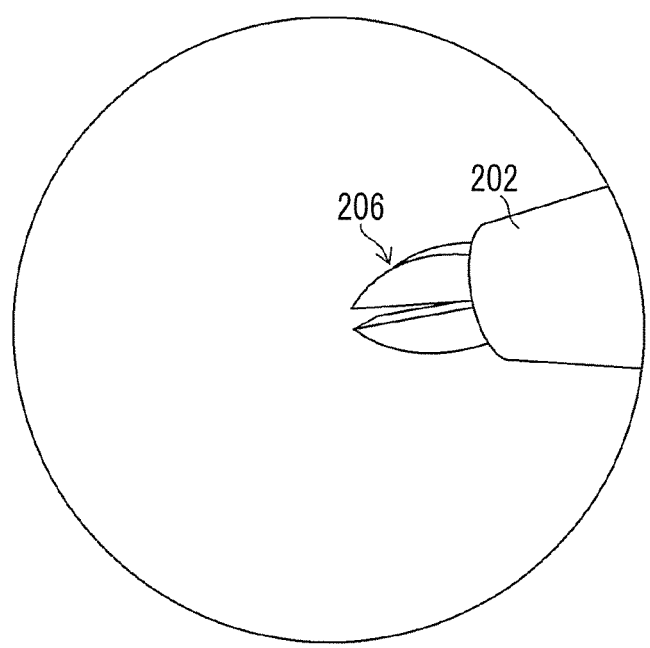
FIG. 9 is a view illustrating an observation image obtained in the state of FIG. 8.

Accordingly, the spacing between the observation part at the distal end of the endoscope insertion part 102 and the treatment part 206 at the distal end of the treatment tool insertion part 202 can be increased, and even in a case where the diameter of the overtube 300 is reduced, dead areas are not easily generated by portions other than the distal end of the treatment part 206, and a portion up to the distal end of the treatment part 206 of the treatment tool insertion part 202 can be visually recognized, as in an observation image illustrated in FIG. 9.

For example, in the standard usage under treatment, the amount of protrusion (the amount of protrusion from the treatment tool delivery port 316 or the distal end surface 304) of the treatment tool insertion part 202 is set to 60 mm, and the amount of protrusion (the amount of protrusion from the endoscope delivery port 312 or the distal end surface 304) of the endoscope insertion part 102 is set to 95 mm. In this case, in order for the portion up to the distal end of the treatment part 206 to be capable of being observed without any dead area on the observation image, it is preferable to incline the endoscope delivery axis 306b with respect to the reference axis 300a so that the center of the observation window 116 is separated from the horizontal reference plane by 4.2 mm.

In addition, in a case where the endoscope delivery axis 306b is made oblique to the endoscope insertion axis 306a (treatment tool insertion axis 308a) as in the present embodiment, the distal end portion of the treatment part 206 is reflected on a peripheral edge on the observation image if a direct viewing type endoscope in which the center of the visual field range is made oblique to an axis direction of the endoscope insertion part 102 is used as the endoscope 100. Although the observation image obtained by the endoscope 100 may be displayed on the monitor 112 as it is, the observation image may be partially cut off and processed so that the distal end portion of the treatment part 206 is located in the vicinity of the center of the observation image, and may be displayed on the monitor 112. In addition, the distal end portion of the treatment part 206 may be reflected in the vicinity of the center of the observation image, using the direct viewing type endoscope in which the center of the visual field range becomes oblique to the axis direction of the endoscope insertion part 102, as the endoscope 100.

Additionally, in a case where the amounts of protrusion of the endoscope insertion part 102 and the treatment tool insertion part 202 that are respectively delivered from the endoscope delivery port 312 and the treatment tool delivery port 316 are small even in a case where the endoscope insertion part 102 inserted through the endoscope insertion passage 306 like the overtube 300 of the present embodiment is delivered obliquely with respect to the treatment tool insertion part 202 inserted through the treatment tool insertion passage 308, the spacing (offset) between the observation part at the distal end of the endoscope insertion part 102 and the treatment part 206 at the distal end of the treatment tool insertion part 202 cannot be sufficiently increased.

However, when the amounts of protrusion of the endoscope insertion part 102 and the treatment tool insertion part 202 are small, treatment is not necessarily performed, and therefore, the offset may be small, and when the amounts of protrusion of the endoscope insertion part 102 and the treatment tool insertion part 202 are large, and a state where treatment is performed is brought about, the offset just has to be provided with a size such that dead areas are not generated by any portions other than the distal end of the treatment part 206.

According to the overtube 300 of the present embodiment, when the amounts of protrusion of the endoscope insertion part 102 and the treatment tool insertion part 202 are small, the offset is small. However, since there is no substantial operational influence from the above-described reason, and the diameter of an overtube 300 can be made small, there is an advantage that invasion is not enlarged. Additionally, since the offset becomes large when the amounts of protrusion of the endoscope insertion part 102 and the treatment tool insertion part 202 are large, the distal end of the treatment part 206 can be visually recognized by the observation image captured by the endoscope 100, and surgical efficiency is improved.

Additionally, it is desirable that an angle at which the endoscope insertion part 102 is obliquely delivered from the endoscope delivery port 312 is within a range of 2 degrees or more and 7 degrees or less. In this case, the movement, in the upward-downward direction or the leftward-rightward direction, of the treatment part 206 in the observation image is little, and it is possible for a surgeon to perform an intuitive operation. Therefore, surgical efficiency does not decline, and it is also possible to see the forceps (treatment part 206) obliquely.

On the other hand, if the angle at which the endoscope insertion part 102 is obliquely delivered from the endoscope delivery port 312 is large, the resistance of sliding with the overtube 300 with respect to the forward and backward movement operation of the endoscope insertion part 102 becomes large. Therefore, it is preferable that the angle is 7 degrees or less as described above.

In addition, if the angle at which the endoscope insertion part 102 is obliquely delivered from the endoscope delivery port 312 obliquely is too small, dead areas may be generated, and if the angle is too large, an abrupt change of the visual field occurs. Therefore, by setting the angle to a range of 2 degrees or more and 7 degrees or less, there are also secondary effects of restraining the abrupt change of the visual field while suppressing generation of dead areas.

Next, the slider 400 illustrated in FIG. 4 will be described. The slider 400 is housed within the cavity part 324 of the overtube body 320, and is supported so as to be movable forward and backward in the direction of the reference axis 300a. The slider 400 is an interlocking member that is coupled to the endoscope insertion part 102 inserted through the endoscope insertion passage 306 and the treatment tool insertion part 202 inserted through the treatment tool insertion passage 308 and that has a dead zone where the forward and backward movement of either the endoscope insertion part 102 or the treatment tool insertion part 202 in the forward-backward direction (axial direction) does not interlock with the movement of the other and a sensing zone where the forward and backward movement of either the endoscope insertion part 102 or the treatment tool insertion part 202 interlocks with the movement of the other. That is, the endoscope insertion part 102 is adapted to interlock with the forward and backward movement of the treatment tool insertion part 202 in the axial direction with play by the slider 400.

Figure 10:
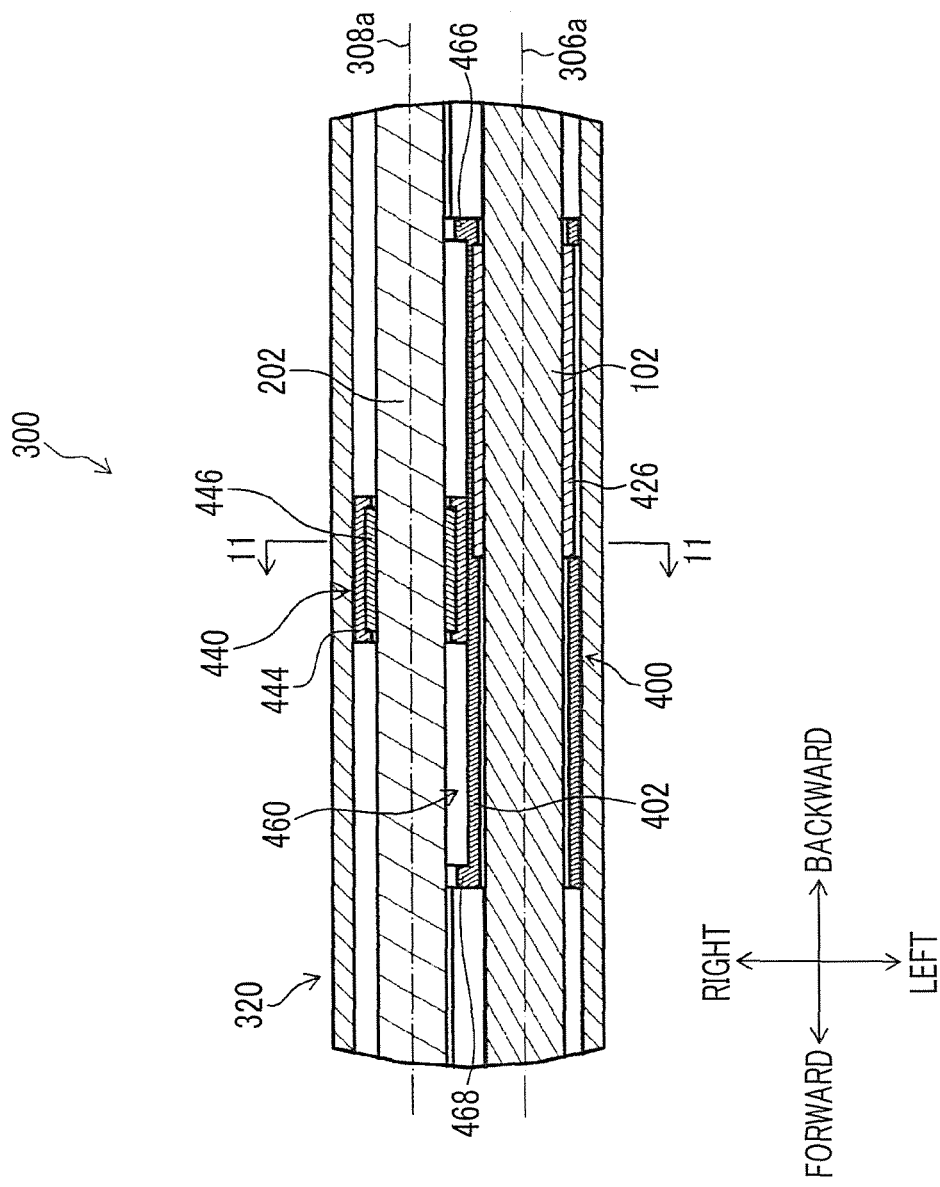
FIG. 10 is an enlarged sectional view illustrating a portion of FIG. 4 in an enlarged manner.
Figure 11:
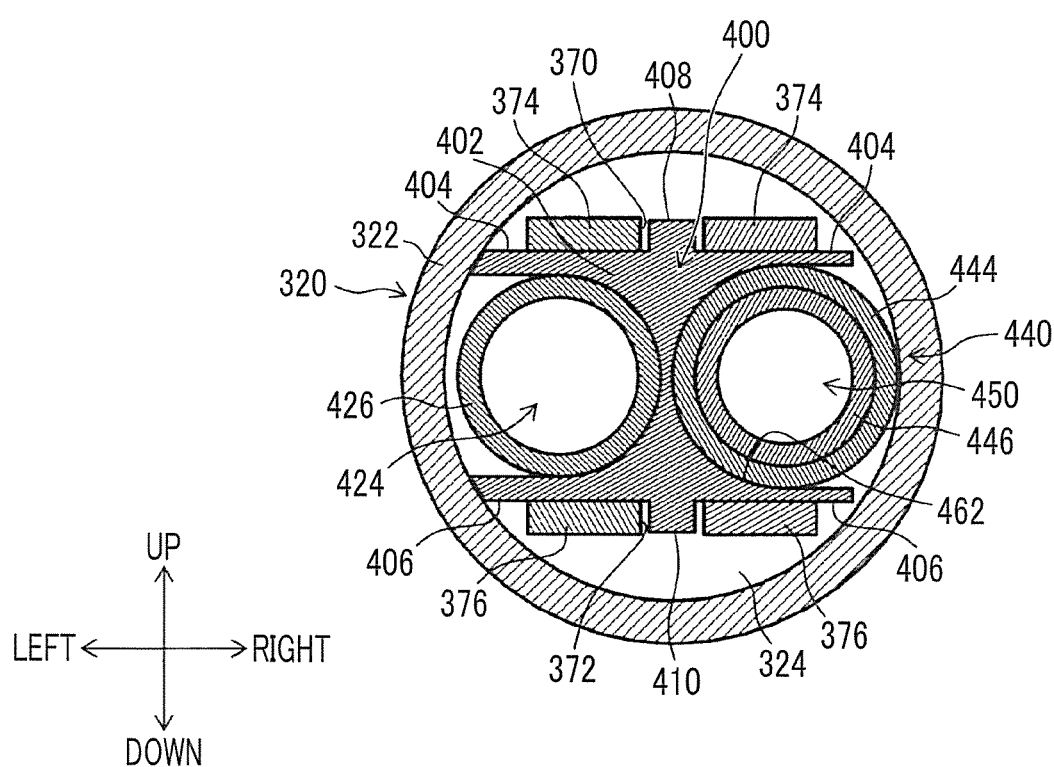
FIG. 11 is a sectional view when viewed from arrow 11-11 in FIG. 10.

FIG. 10 is an enlarged sectional view illustrating a portion, in which the slider 400 is arranged in FIG. 4, in an enlarged manner, and illustrates a state where the endoscope insertion part 102 and the treatment tool insertion part 202 have been inserted through the endoscope insertion passage 306 and the treatment tool insertion passage 308, respectively. FIG. 11 is a sectional view when viewed from arrow 11-11 in FIG. 10.

As illustrated in FIGS. 10 and 11, the slider 400 has a slider body 402 (slider member) that holds components of the slider 400. As illustrated in FIG. 11, protruding strips 408 and 410 that extend in the direction (forward-backward direction) of the reference axis 300a are formed on a flat upper surface 404 and a flat lower surface 406 of the slider body 402.

Meanwhile, a pair of left and right long plate-shaped guide plates 374 and 374 and a pair of left and right long plate-shaped guide plates 376 and 376, which are laid between the base end cap 340 and the distal end cap 360, are respectively supported by an upper part and a lower part within the cavity part 324 of the overtube body 320, and guide grooves 370 and 372, which extend in the direction of the reference axis 300a from the base end cap 340 to the distal end cap 360, are formed by a gap between the guide plates 374 and 374 and a gap between the guide plates 376 and 376.

The protruding strips 408 and 410 of the slider body 402 are respectively fitted into the guide grooves 370 and 372 within the cavity part 324, and the upper surface 404 and the lower surface 406 are arranged in a state where these surfaces have contacted or approached the guide plates 374 and 374 and the guide plates 376 and 376.

Accordingly, the slider 400 is supported so as to be movable forward and backward in the forward-backward direction within the cavity part 324, and is supported in a state where the movement of the slider in the upward-downward direction and in the leftward-rightward direction and the rotation of the slider in all directions (directions around three axes including a forward-backward axis, a leftward-rightward axis, and an upward-downward direction) are restricted. Additionally, the slider 400 moves forward and backward within a movable range having a position where the slider abuts against the base end cap 340 as a rear end, and having a position where the slider abuts against the distal end cap 360 as a front end.

In addition, the guide grooves 370 and 372 may not be formed by the guide plates 374 and 374 and the guide plates 376 and 376 arranged within the cavity part 324 of the overtube body 320, and may be formed in the outer wall 322 of the overtube body 320 or may be formed by other configurations.

Additionally, the slider 400, as illustrated in FIG. 4, has an endoscope-coupled part 420 that is coupled (engaged) with the endoscope insertion part 102, and a treatment tool-coupled part 422 that is coupled (engaged) with the treatment tool insertion part 202. In addition, the endoscope-coupled part 420 is equivalent to a first coupling part, and the treatment tool-coupled part 422 is equivalent to a second coupling part.

The endoscope-coupled part 420 is provided on the left side of the slider body 402, and includes a through-hole 424

(refer to FIG. 11) in which a space serving as the endoscope insertion passage 306 is secured within the cavity part 324 of the overtube body 320 and through which, as illustrated in FIG. 10, the endoscope insertion part 102 is inserted, and a pressure-contact member 426 that is fixed to the through-hole 424, is brought into pressure contact with the outer peripheral surface (side surface) of the endoscope insertion part 102 inserted through the endoscope insertion passage 306. The pressure-contact member 426 is annularly formed of elastic materials, such as elastic rubber, as illustrated in FIG. 11.

Accordingly, when the endoscope insertion part 102 has been inserted through the endoscope insertion passage 306, as illustrated in FIG. 10, the endoscope insertion part 102 is inserted through the through-hole 424, the pressure-contact member 426 is brought into pressure contact with (engaged with) the outer peripheral surface of the endoscope insertion part 102, and the central axis of the endoscope insertion part 102 is arranged coaxially with the endoscope insertion axis 306a.

The endoscope insertion part 102 and the slider 400 (slider body 402) are coupled (engaged) with each other in an interlockable manner via the pressure-contact member 426, and the slider 400 (slider body 402) also integrally moves forward and backward in an interlocking manner with the forward and backward movement of the endoscope insertion part 102 in the forward-backward direction (axial direction).

In addition, since the coupling herein is based on the elastic force of the pressure-contact member 426, the engagement position (the position of the endoscope insertion part 102 where the slider 400 is engaged) of the endoscope insertion part 102 coupled to the slider 400 (slider body 402) can be arbitrarily adjusted.

The treatment tool-coupled part 422, as illustrated in FIG. 4, is provided on the right side of the slider body 402, and as illustrated in FIG. 10, includes a sleeve 440 (sleeve member) that is coupled to the treatment tool insertion part 202, and a guide part 460 that guides the sleeve 440 so as to be movable forward and backward in the forward-backward direction.

The sleeve 440, as illustrated in FIG. 11, includes a sleeve body (frame body) 444 formed in a cylindrical shape, and a pressure-contact member 446 fixed to the inside of the sleeve body 444. The pressure-contact member 446 is annularly formed of elastic materials, such as elastic rubber.

Accordingly, when the treatment tool insertion part 202 has been inserted through the treatment tool insertion passage 308, as illustrated in FIG. 10, the treatment tool insertion part 202 is inserted through the inside (the through-hole 450 of FIG. 11) of the pressure-contact member 446, the pressure-contact member 446 is brought into pressure contact with (engaged with) the outer peripheral surface of the treatment tool insertion part 202, and the central axis of the treatment tool insertion part 202 is arranged coaxially with the treatment tool insertion axis 308a. The treatment tool insertion part 202 and the sleeve 440 are coupled with each other in an interlockable manner via the pressure-contact member 446, and the sleeve 440 also integrally moves forward and backward in an interlocking manner with the forward and backward movement of the treatment tool insertion part 202 in the forward-backward direction (axial direction).

Additionally, the sleeve 440 also rotates with respect to the slider body 402 in an interlocking manner with the rotation of the treatment tool insertion part 202 around the axis thereof.

In addition, since the coupling between the treatment tool insertion part 202 and the sleeve 440 herein is based on the elastic force of the pressure-contact member 446, the engagement position (the position of the treatment tool insertion part 202 where the sleeve 440 is engaged) of the treatment tool insertion part 202 coupled to the sleeve 440 can be arbitrarily adjusted.

Meanwhile, the guide part 460 of the treatment tool-coupled part 422, as illustrated in FIG. 11, is formed by a space surrounded by a guide surface 462 of the slider body 402 that extends in the direction of the reference axis 300a within the cavity part 324 of the overtube body 320, and an inner peripheral surface of the overtube body 320. The sleeve 440 is housed and arranged in the space of the guide part 460, is supported so as to be movable in the forward-backward direction and rotatable around its axis, and is supported in a state where the movement of the sleeve in the upward-downward direction and in the leftward-rightward direction is restricted.

Additionally, the guide part 460 is provided so as to fall within a range from a base end of the slider body 402 to a distal end thereof, and as illustrated in FIG. 10, has end edge parts 466 and 468, which are formed to protrude in a direction orthogonal to the guide surface 462 along an end edge of the guide surface 462, respectively, on the base end side and the distal end side of the slider body 402.

The end edge parts 466 and 468 abut against the end of the sleeve 440 to restrict the movement of the sleeve 440, when the sleeve 440 arranged in the space of the guide part 460 moves forward and backward in the forward-backward direction.

Therefore, the sleeve 440 moves forward and backward within a movable range having a position where the sleeve abuts against the end edge part 466 as a rear end, and having a position where the sleeve abuts against the end edge part 468 as a front end. However, the rear end and the front end of the movable range of the sleeve 440 may not be restricted by the end edge part 466 and the end edge part 468.

According to the slider 400 configured as described above, the endoscope insertion part 102 inserted through the endoscope insertion passage 306 of the overtube 300 and the slider body 402 are coupled together, and the treatment tool insertion part 202 inserted through the treatment tool insertion passage 308 of the overtube 300 and the sleeve 440 are coupled together.

Figure 12:
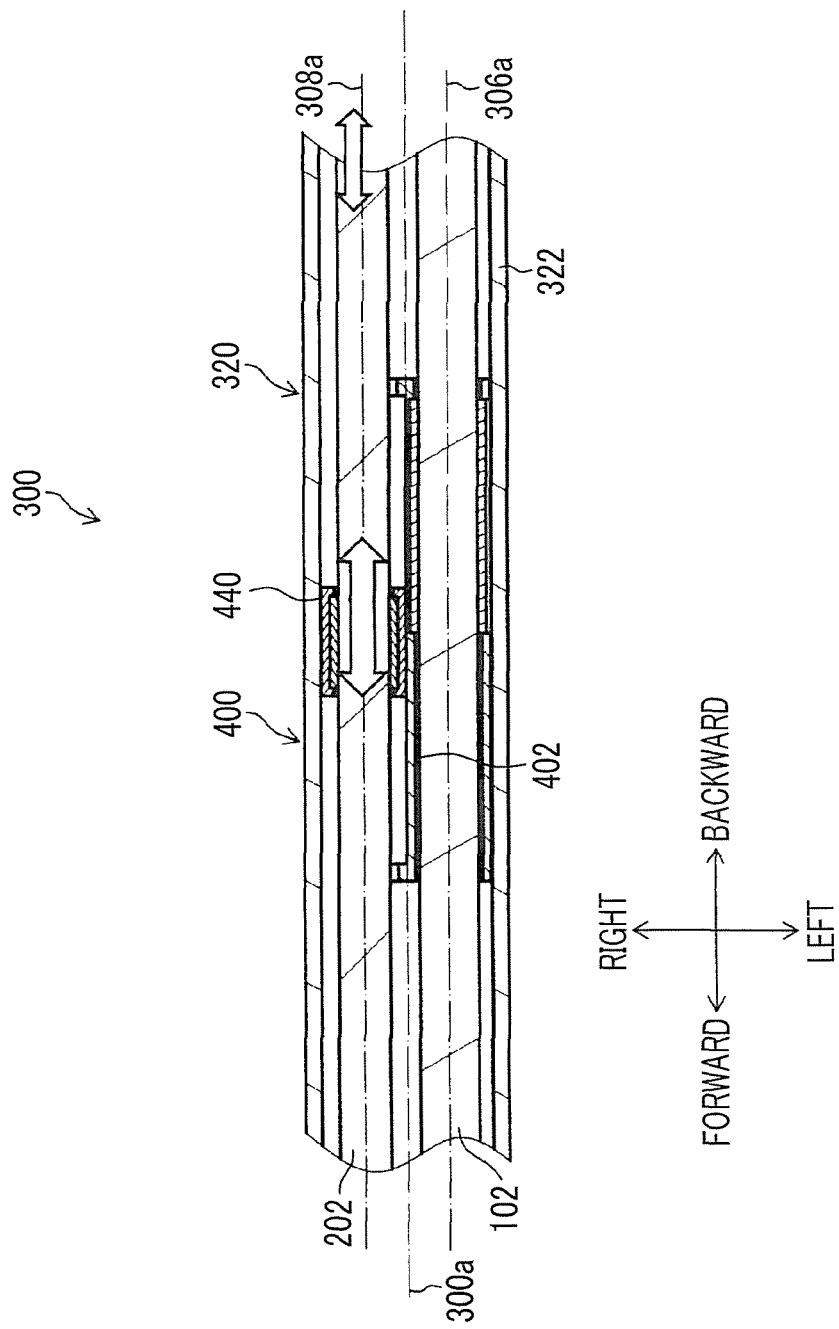
FIG. 12 is an explanatory view used for the description of the action of a slider.

As illustrated in FIG. 12, it is supposed that a surgeon performs a forward and backward movement operation for moving the treatment tool insertion part 202 forward and backward in the axial direction (forward-backward direction) in a state where the sleeve 440 has not reached the rear end and the front end of the movable range thereof with respect to the slider body 402 (guide part 460).

In this case, in a case where the sleeve 440 has moved forward and backward within the movable range thereof with respect to the slider body 402, the slider body 402 does not move with respect to the forward and backward movement of the treatment tool insertion part 202. Therefore, a forward and backward movement operation in the dead zone where the endoscope insertion part 102 does not interlock with the forward and backward movement of the treatment tool insertion part 202 is performed.

Figure 13:
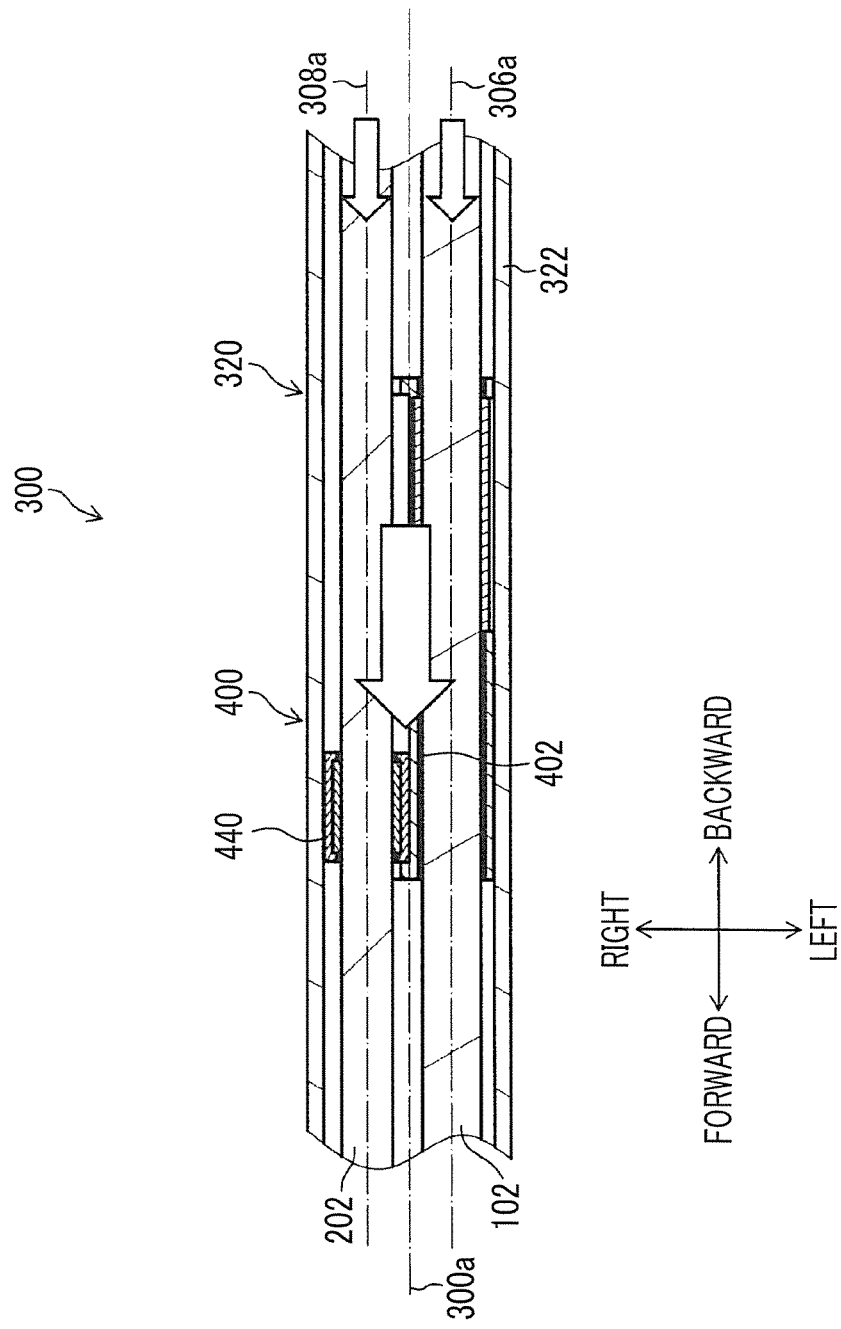
FIG. 13 is an explanatory view used for the description of the action of the slider.

Meanwhile, as illustrated in FIG. 13, if the treatment tool insertion part 202 is operated to move forward in a state where the sleeve 440 reaches the front end of the movable range thereof with respect to the slider body 402, the sleeve 440 and the slider body 402 move forward with respect to the overtube body 320 together with the treatment tool insertion part 202. Accordingly, a forward and backward movement operation in the sensing zone where the endoscope insertion part 102 moves forward in an interlocking manner with the treatment tool insertion part 202 is performed.

Figure 14:
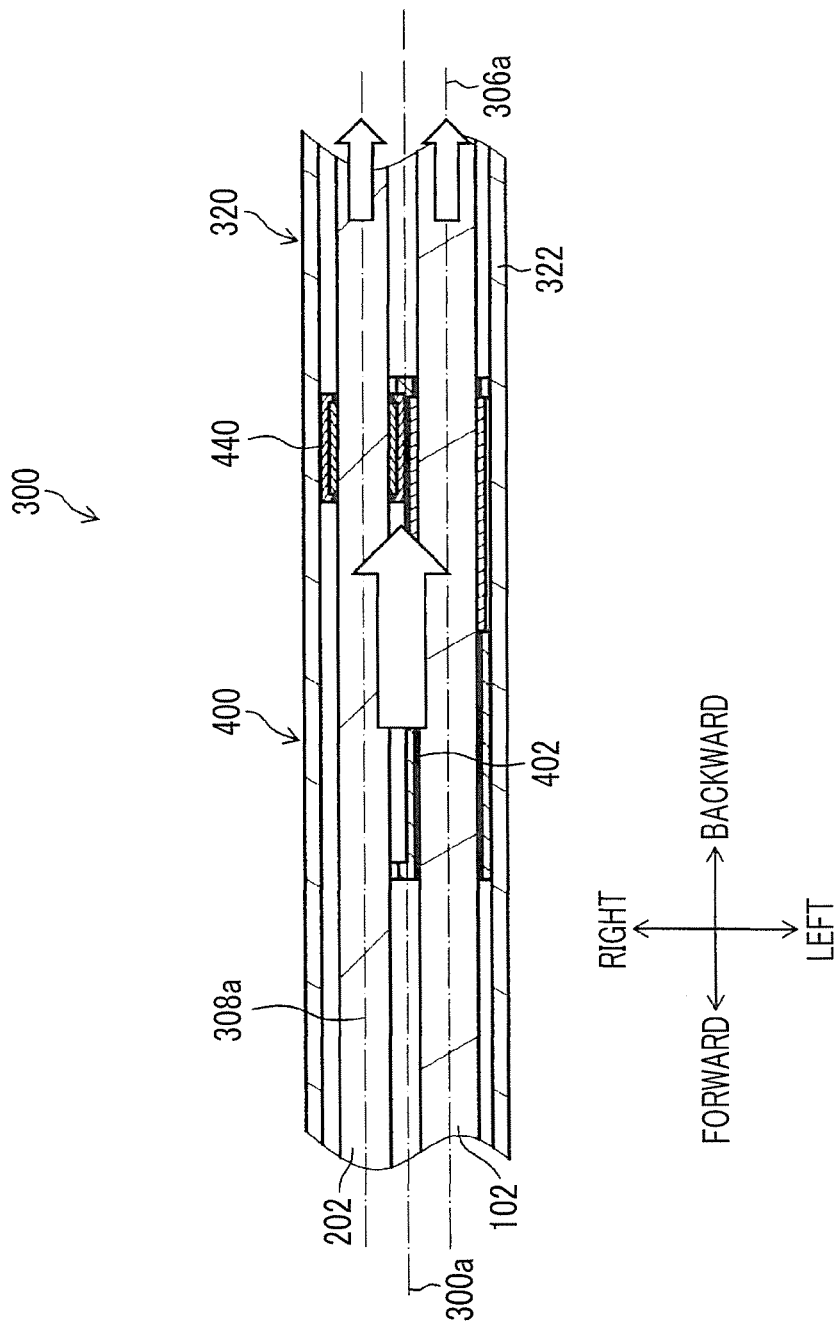
FIG. 14 is an explanatory view used for the description of the action of the slider.

Similarly, as illustrated in FIG. 14, if the treatment tool insertion part 202 is operated to move backward in a state where the sleeve 440 reaches the rear end of the movable range thereof with respect to the slider body 402, the sleeve 440 and the slider body 402 move backward with respect to the overtube body 320 together with the treatment tool insertion part 202. Accordingly, a forward and backward movement operation in the sensing zone where the endoscope insertion part 102 moves backward in an interlocking manner with the treatment tool insertion part 202 is performed.

As described above, according to the slider 400 of the present embodiment, in a case where the forward and backward movement operation (the forward and backward movement operation in the sensing zone) of the treatment tool insertion part 202 is performed, the endoscope insertion part 102 is displaced in the axial direction in an interlocking manner with the treatment tool insertion part 202, and in a case where a small amplitude of forward and backward movement operation (the forward and backward movement operation in the dead zone) of the treatment tool insertion part 202 is performed, the endoscope insertion part 102 is not displaced in the axial direction.

Accordingly, in a case where a surgeon has operated to move the treatment tool insertion part 202 forward and backward in the axial direction, the endoscope insertion part 102 also moves forward and backward in an interlocking manner in the forward-backward direction, in the upward-downward direction, and in the rightward-leftward direction when a large amplitude of forward and backward movement operation is performed. Thus, the visual field, orientation, and the like of the endoscope 100 can be changed as intended by the surgeon. Additionally, the visual field is always given to pick up an image of the distal end of the treatment tool 200 and consequently, an image that is optimal for treatment is automatically provided. In a case where it is desired to check sites other than a site to be treated, the checking can be performed by moving the treatment tool insertion part 202, and a surgeon can perform operations as desired. Therefore, an assistant (endoscopic technician) who operates the endoscope 100 apart from the surgeon can be made unnecessary, and a troublesome condition in which the surgeon should instruct an assistant about the visual field, orientation, and the like of the endoscope 100 serially can be eliminated.

Additionally, when a small amplitude of forward and backward movement operation of the treatment tool insertion part 202 has been performed, the endoscope insertion part 102 does not interlock. Therefore, the size of an object to be observed within an observation image can be prevented from fluctuating unnecessarily, a sense of perspective can be suitably maintained, and a stable observation image can be provided.

Moreover, the delivery direction of the endoscope insertion part 102 delivered from the distal end of the overtube 300 is oblique to the delivery direction of the treatment tool insertion part 202, and the line of sight of the endoscope 100 becomes a direction oblique to the forward and backward movement directions of the treatment tool insertion part 202. Accordingly, when the treatment part 206 of the treatment tool 200 approaches a living body tissue within a body cavity, dead areas are not easily generated by portions other than the distal end of the treatment part 206, it is possible to easily check the state of the distal end of the treatment part 206 while suitably maintaining a sense of perspective, and operability can be improved.

In addition, the sleeve 440 is rotatable with respect to the slider body 402 around its axis. Therefore, in a case where the treatment tool insertion part 202 has been operated to rotate around its axis, the treatment tool insertion part 202 can also be rotated around its axis together with the sleeve 440 without rotating the slider body 402 (without changing the positional relationship (position within the body cavity) of the endoscope insertion part 102 and the treatment tool insertion part 202 with respect to the overtube 300).

Next, an example of the forward and backward movement operation of the endoscope 100 and the treatment tool 200 in the endoscopic surgical device 10 of the present embodiment will be described.

FIGS. 15A to 16C are explanatory views illustrating aspects of the operation when treatment of a diseased site within a patient's body cavity is performed using the endoscopic surgical device 10 of the present embodiment, FIGS. 15A to 15C illustrate an aspect of the operation (the forward and backward movement operation in the dead zone) when only the treatment tool 200 moves forward and backward, and FIGS. 16A to 16C illustrate an aspect of the operation (forward and backward movement operation in the sensing zone) when the treatment tool 200 moves forward and backward in an interlocking manner with the endoscope 100.

As illustrated in FIG. 15A, the endoscope 100 (endoscope insertion part 102) and the treatment tool 200 (treatment tool insertion part 202) are respectively inserted into the endoscope insertion passage 306 and the treatment tool insertion passage 308 of the overtube 300 after the overtube 300 is inserted into a patient's body wall and a pneumoperitoneum gas is injected into a body cavity. In this case, the endoscope 100 is coupled to the slider body 402 of the slider 400, and the treatment tool 200 is coupled to the sleeve 440 of the slider 400. Thus, when the sleeve 440 moves within a movable range thereof with respect to the slider body 402, the interlocking is performed with the dead zone (play) where the endoscope 100 does not interlock with the forward and backward movement of the treatment tool 200.

In this state, if the surgeon grips the operating part 204 of the treatment tool 200 and minutely moves the treatment tool 200 forward, only the treatment tool 200 moves forward in a state where the endoscope 100 is stationary as illustrated in FIG. 15B, with respect to the forward movement in the dead zone until the sleeve 440 of the slider 400 abuts against the front end of the movable range thereof.

Similarly, if the surgeon grips the operating part 204 of the treatment tool 200 and minutely moves the treatment tool 200 backward, only the treatment tool 200 moves backward in a state where the endoscope 100 is stationary as illustrated in FIG. 15C, with respect to the backward movement in the dead zone until the sleeve 440 of the slider 400 abuts against the rear end of the movable range thereof.

Therefore, since the endoscope 100 does not move forward and backward with respect to the minute forward and backward movement operation of the treatment tool 200, that is, the forward and backward movement operation thereof in the dead zone, the range of an observation image displayed on the monitor 112 does not change, the size of an object to be observed can be prevented from fluctuating according to the minute displacement of the treatment tool 200, a sense of perspective can be suitably maintained, and a stable observation image can be obtained.

FIG. 16A illustrates that the overtube 300, the endoscope 100, and the treatment tool 200 are in the same state as those of FIG. 15A.

In this state, if the surgeon grips the operating part 204 of the treatment tool 200 and greatly moves the treatment tool 200 forward, the endoscope 100 moves forward in an interlocking manner with the forward movement of the treatment tool 200 through an interlocking function of the slider 400 as illustrated in FIG. 16B, after the forward movement in the dead zone until the sleeve 440 of the slider 400 abuts against the front end of the movable range.

Similarly, if the surgeon grips the operating part 204 of the treatment tool 200 and greatly moves the treatment tool 200 backward, the endoscope 100 moves backward in an interlocking manner with the backward movement of the treatment tool 200 through an interlocking function of the slider 400 as illustrated in FIG. 16C, after the backward movement in the dead zone until the sleeve 440 of the slider 400 abuts against the rear end of the movable range.

Therefore, since the endoscope 100 moves forward and backward with respect to a large forward and backward movement operation of the treatment tool 200, that is, the forward and backward movement operation thereof in the sensing zone, the range of an observation image displayed on the monitor 112 is continuously changed so as to follow the forward and backward movement of the treatment tool 200. Accordingly, since the size of an object to be observed changes according to the operation of the treatment tool 200, an image desired by a surgeon can be simply obtained.

As described above, in the overtube 300 of the above embodiment, the guide part 384 of the endoscope delivery port 312 illustrated in FIG. 5 can also be a movable guide part so that the delivery direction of the endoscope insertion part 102 from the endoscope delivery port 312 is variable.

A form in this case is illustrated in FIG. 17 illustrating a portion of the distal end cap 360 of the overtube 300 in an enlarged manner. In addition, constituent elements having the same or similar functions as those of the constituent elements illustrated in FIG. 5 will be designated by the same reference signs and the description thereof will be omitted.

As illustrated in this drawing, a through-hole 362 through which the endoscope insertion part 102 is inserted along the direction of the endoscope insertion axis 306a is formed in the distal end cap 360, and a space communicating with the right through-hole 362 is provided with a stand 390 serving as the movable guide part.

The stand 390 is supported so as to be turnable around a rotating shaft 392 parallel to the upward-downward direction on a rear end side. Additionally, the stand 390 is coupled with an operating part (not illustrated) that is provided in the base end cap 340 of the overtube 300, or the like, for example by an operating wire inserted through the inside of the overtube body 320, so that a surgeon can adjust the rotational angle of the stand 390 around the rotating shaft 392 to a desired angle through the operation of the operating part. The amount of protrusion of the stand 390 into the through-hole 362 can be adjusted by adjusting the rotational angle of the stand 390 around the rotating shaft 392. Accordingly, the delivery direction of the distal end of the endoscope insertion part 102 is made variable, for example, between a straight-ahead direction parallel to the treatment tool insertion passage 308, and an oblique directions away from the treatment tool insertion passage 308.

According to this, the delivery direction (delivery angle) of the endoscope insertion part 102 from the endoscope delivery port 312 can be appropriately made variable by adjusting the amount of protrusion of the stand 390 into the through-hole 362. Additionally, the adjustment of the amount of protrusion of the stand 390 (the adjustment of the delivery direction of the endoscope insertion part 102) can be performed at an arbitrary timing after the endoscope insertion part 102 is inserted through the endoscope insertion passage 306 of the overtube 300. Therefore, when the operation at the time of the insertion of inserting the endoscope insertion part 102 through the endoscope insertion passage 306, the forward and backward movement operation of the endoscope insertion part 102 inserted through the endoscope insertion passage 306, and the like are performed, these operations can be easily performed by withdrawing the stand 390 in a state where the stand does not come into contact with the endoscope insertion part 102.

Additionally, the endoscope 100 in which the overall tubular body of the outer peripheral part of the endoscope insertion part 102 is formed of an elastic body is used in the above embodiment. However, an endoscope may be used in which only the portion of the tubular body where bending on the distal end side of the endoscope insertion part 102 is required is constituted of an elastic body (at least a portion delivered into a body cavity from the endoscope delivery port 312 is constituted of the elastic body) and the portion of the tubular body on the base end side is formed of materials (hard resins, metals, or the like) that is difficult in bending).

Additionally, the overall tubular body of the outer peripheral part of the endoscope insertion part 102 or only the portion of the tubular body where the bending on the distal end side is required just has to have flexibility even if these does not have elasticity. However, if there is no elasticity, the resistance of sliding with the guide part (the guide part 384 or the stand 390) becomes small. However, there is a concern that the distal end portion delivered from the endoscope delivery port 312 protrudes in a circular-arc shape, and deviation of the line of sight may become too large. Therefore, it is preferable to have not only flexibility but elasticity. In a case where elasticity is not provided, the resistance of sliding with the guide part becomes large, but the distal end portion delivered from the endoscope delivery port 312 protrudes linearly. Therefore, the deviation of the line of sight can be restrained from becoming too large.

Additionally, in the above embodiment, the guide part (the guide part 384 or the stand 390) that guides the distal end of the endoscope insertion part 102 inserted through the endoscope insertion passage 306 of the overtube 300 in the direction away from the distal end of the treatment tool insertion part 202 is provided in the endoscope insertion passage 306. However, the treatment tool insertion passage 308 may be provided with the guide part, and the distal end of the treatment tool insertion part 202 inserted through the treatment tool insertion passage 308 of the overtube 300 may be guided in the direction away from the distal end of the endoscope insertion part 102. That is, an insertion passage provided with the guide part out of a first insertion passage of the overtube 300 through which the first insertion part of the first medical instrument is inserted, and a second insertion passage of the overtube 300 through which the second insertion part of the second medical instrument is inserted is referred to as the first insertion passage. In this case, the invention is not limited to a case where the first insertion passage is an insertion passage through which the endoscope insertion part 102 is inserted and the second insertion passage is an insertion passage through which treatment tool insertion part 202 is inserted, as in the above embodiment. The first insertion passage may be an insertion passage through which the treatment tool insertion part 202 is inserted, and the second insertion passage may be an insertion passage through which the endoscope insertion part 102 is inserted.

EXPLANATION OF REFERENCES

10: endoscopic surgical device
100: endoscope
102: endoscope insertion part
104: cable part
108: processor device
110: light source device
112: monitor
116: observation window
118: illumination window
200: treatment tool
202: treatment tool insertion part
204: operating part
206: treatment part
300: overtube
300a: reference axis
306: endoscope insertion passage
306a: endoscope insertion axis
306b: endoscope delivery axis
308: treatment tool insertion passage
308a: treatment tool insertion axis
310: endoscope insertion port
312: endoscope delivery port
314: treatment tool insertion port
316: treatment tool delivery port
320: overtube body
340: base end cap
360: distal end cap
362, 364: through-hole
380: straight hole
382: guide hole
384: guide part
386: cutout part
390: stand
392: rotating shaft
400: slider
402: slider body
420: endoscope-coupled part
422: treatment tool-coupled part
440: sleeve

What is claimed is:

1. An endoscopic surgical device comprising:
    a first medical instrument having a first insertion part to be inserted into a body cavity;
    a second medical instrument having a second insertion part to be inserted into the body cavity; and
    an overtube that guides the first insertion part and the second insertion part into the body cavity in a distal direction,
    wherein the overtube includes
    an overtube body that passes through a body wall and is inserted into the body cavity,
    a first insertion passage that is provided inside the overtube body and allows the first insertion part to be inserted therethrough so as to be movable forward and backward,
    a second insertion passage that is provided inside the overtube body and allows the second insertion part to be inserted therethrough so as to be movable forward and backward,
    a sleeve coupled to the second insertion part inserted through the second insertion passage; and
    a slider coupled to the first insertion part inserted through the first insertion passage, the slider being arranged inside the overtube body so as to be movable forward and backward,
    wherein the slider includes a first stopper and a second stopper along a forward and backward moving direction of the slider, wherein the sleeve is configured to move between the first and second stoppers, wherein a forward and backward movement of either the first insertion part or the second insertion part does not interlock with the movement of the other when the sleeve moves between the first and second stoppers, and the forward and backward movement of either the first insertion part or the second insertion part interlocks with the movement of the other when the sleeve abuts against the first stopper or the second stopper of the slider, and
    wherein the first insertion passage is provided with a through-hole located on a distal end cap of the overtube, and the through-hole causes a distal end of the first insertion part to move in a direction away from a distal end of the second insertion part when the distal end of the first insertion part moves toward the distal direction.

2. The endoscopic surgical device according to claim 1, wherein the first medical instrument is an endoscope in which an observation part is provided at the distal end of the first insertion part, and
    wherein the second medical instrument is a treatment tool in which a treatment part is provided at the distal end of the second insertion part.

3. The endoscopic surgical device according to claim 1, wherein the through-hole includes an inclined part that is provided to protrude toward the inside of the first insertion passage, and the inclined part includes a guide surface that guides a delivery direction of the distal end of the first insertion part delivered from the first insertion passage in an oblique direction away from the second insertion passage.

4. The endoscopic surgical device according to claim 1, wherein the through-hole includes a movable guide part that allows a delivery direction of the distal end of the first insertion part delivered from the first insertion passage to be variable between a straight-ahead direction parallel to the second insertion passage and an oblique direction away from the second insertion passage.

5. The endoscopic surgical device according to claim 1, wherein at least a portion of the first insertion part delivered into the body cavity from the distal end of the first insertion passage has flexibility.

6. The endoscopic surgical device according to claim 5, wherein the portion delivered into the body cavity has elasticity.

7. An overtube used in an endoscopic surgical device including a first medical instrument having a first insertion part to be inserted into a body cavity, a second medical instrument having a second insertion part to be inserted into the body cavity, and the overtube that guides the first insertion part and the second insertion part into the body cavity in a distal direction, the overtube comprising:
    an overtube body that passes through a body wall and is inserted into the body cavity;
    a first insertion passage that is provided inside the overtube body and allows the first insertion part to be inserted therethrough so as to be movable forward and backward;

a second insertion passage that is provided inside the overtube body and allows the second insertion part to be inserted therethrough so as to be movable forward and backward;

a sleeve configured to be coupled to the second insertion part inserted through the second insertion passage; and a slider configured to be coupled to the first insertion part inserted through the first insertion passage, the slider being arranged inside the overtube body so as to be movable forward and backward, wherein the slider includes a first stopper and a second stopper along a forward and backward moving direction of the slider, wherein the sleeve is configured to move between the first and second stoppers, wherein a forward and backward movement of either the first insertion part or the second insertion part does not interlock with the movement of the other when the sleeve moves between the first and second stoppers, and the forward and backward movement of either the first insertion part or the second insertion part interlocks with the movement of the other when the sleeves abuts against the first stopper or the second stopper of the slider, and wherein the first insertion passage is provided with through-hole located on a distal end cap of the overtube, and the through-hole is configured to cause a distal end of the first insertion part to move in a direction away from a distal end of the second insertion part when the distal end of the first insertion part moves toward the distal direction.

8. The overtube according to claim 7, wherein the first medical instrument is an endoscope in which an observation part is provided at the distal end of the first insertion part, and wherein the second medical instrument is a treatment tool in which a treatment part is provided at the distal end of the second insertion part.

9. The overtube according to claim 7, wherein the through-hole includes an inclined part that is provided to protrude toward the inside of the first insertion passage, and the inclined part includes a guide surface that is configured to guide a delivery direction of the distal end of the first insertion part delivered from the first insertion passage in an oblique direction away from the second insertion passage.

10. The overtube according to claim 7, wherein the through-hole includes a movable guide part that allows a delivery direction of the distal end of the first insertion part delivered from the first insertion passage to be variable between a straight-ahead direction parallel to the second insertion passage and an oblique direction away from the second insertion passage.

11. The overtube according to claim 7, wherein at least a portion of the first insertion part delivered into the body cavity from the distal end of the first insertion passage has flexibility.

12. The overtube according to claim 11, wherein the portion delivered into the body cavity has elasticity.

* * * * *